United States Patent [19]

Nappholz et al.

[11] Patent Number: 5,183,040
[45] Date of Patent: Feb. 2, 1993

[54] APPARATUS AND METHOD FOR DETECTING ABNORMAL CARDIAC RHYTHMS USING AN ULTRASOUND SENSOR IN AN ARRHYTHMIA CONTROL SYSTEM

[75] Inventors: Tibor A. Nappholz; Ken Koestner, both of Englewood; Harry L. Valenta, Jr., Aurora, all of Colo.

[73] Assignee: Telectronics Pacing Systems, Inc., Englewood, Colo.

[21] Appl. No.: 665,842

[22] Filed: Mar. 8, 1991

[51] Int. Cl.⁵ .............................................. A61N 1/00
[52] U.S. Cl. ........................ 128/419 PG; 128/661.07; 128/661.04; 128/660.03
[58] Field of Search ....... 128/419 D, 419 PG, 661.07, 128/661.08, 661.09, 661.10, 662.05, 661.04, 660.03

[56] References Cited

U.S. PATENT DOCUMENTS

| | | | |
|---|---|---|---|
| 3,857,398 | 12/1974 | Rubin | 128/419 D |
| 4,202,340 | 5/1980 | Langer et al. | 128/419 D |
| 4,291,699 | 9/1981 | Geddes et al. | 178/419 D |
| 4,319,580 | 3/1982 | Colley et al. | 128/661 |
| 4,429,697 | 2/1984 | Nappholz et al. | 128/419 PG |
| 4,475,551 | 10/1984 | Langer | 128/419 D |
| 4,706,681 | 11/1987 | Breyer et al. | 128/661.04 |
| 4,708,143 | 11/1987 | Schroeppel | 128/419 D |
| 4,790,322 | 12/1988 | Iinuma | 128/661.1 |
| 4,821,731 | 4/1989 | Martinelli et al. | 128/660.03 |
| 4,869,252 | 9/1989 | Gilli | 128/419 D |
| 4,901,725 | 2/1990 | Nappholz et al. | 128/419 PG |
| 4,917,115 | 4/1990 | Flammang et al. | 128/661.07 |
| 4,936,304 | 6/1990 | Kresh et al. | 128/419 PG |
| 4,940,054 | 7/1990 | Grevis et al. | 128/419 PG |
| 5,058,583 | 10/1991 | Geddes et al. | 128/419 PG |

OTHER PUBLICATIONS

Fisher, et al., "Termination of Ventricular Tachycardia With Burst or Rapid Ventricular Pacing," American Journal of Cardiology, vol. 41, pp. 94–102 (Jan. 1978).

Primary Examiner—Francis Jaworski
Assistant Examiner—George Manuel
Attorney, Agent, or Firm—Gottlieb, Rackman & Reisman

[57] ABSTRACT

An antitachycardia pacer and pacing method automatically monitors and supports a patient's hemodynamic status by measuring cardiac output using an ultrasonic sensor. By analyzing cardiac output, the pacer determines whether the heart is beating normally or under conditions of exercise, bradycardia, tachycardia, or fibrillation. If the heart is functioning normally or in bradycardia or exercise, the pacer supports the patient's hemodynamic status by electrically stimulating the heart. The pacer analyzes cardiac output information, detects and classifies abnormal rhythms of tachycardia and fibrillation on the basis of this analysis, and initiates an appropriate therapy accordingly.

34 Claims, 13 Drawing Sheets

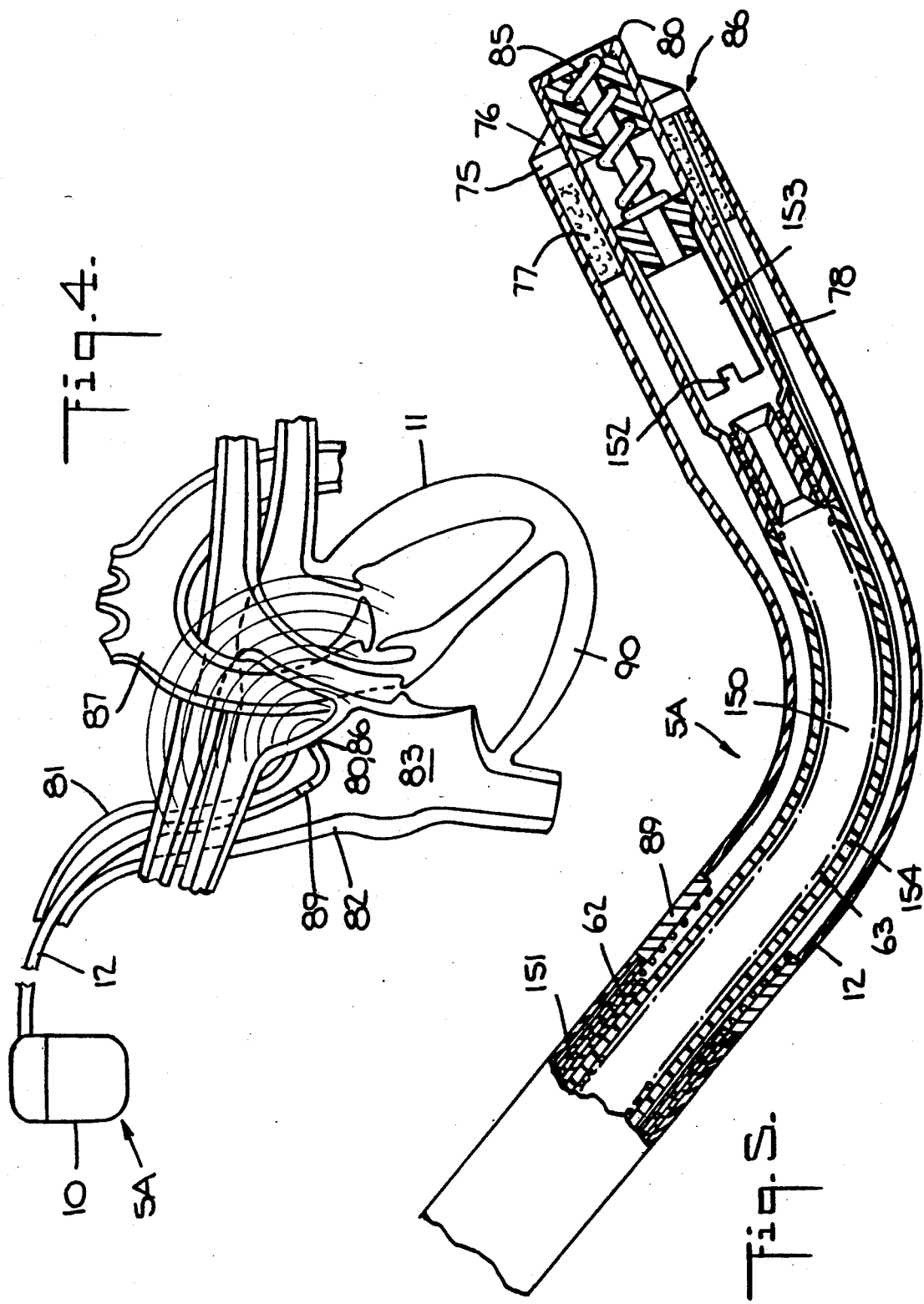

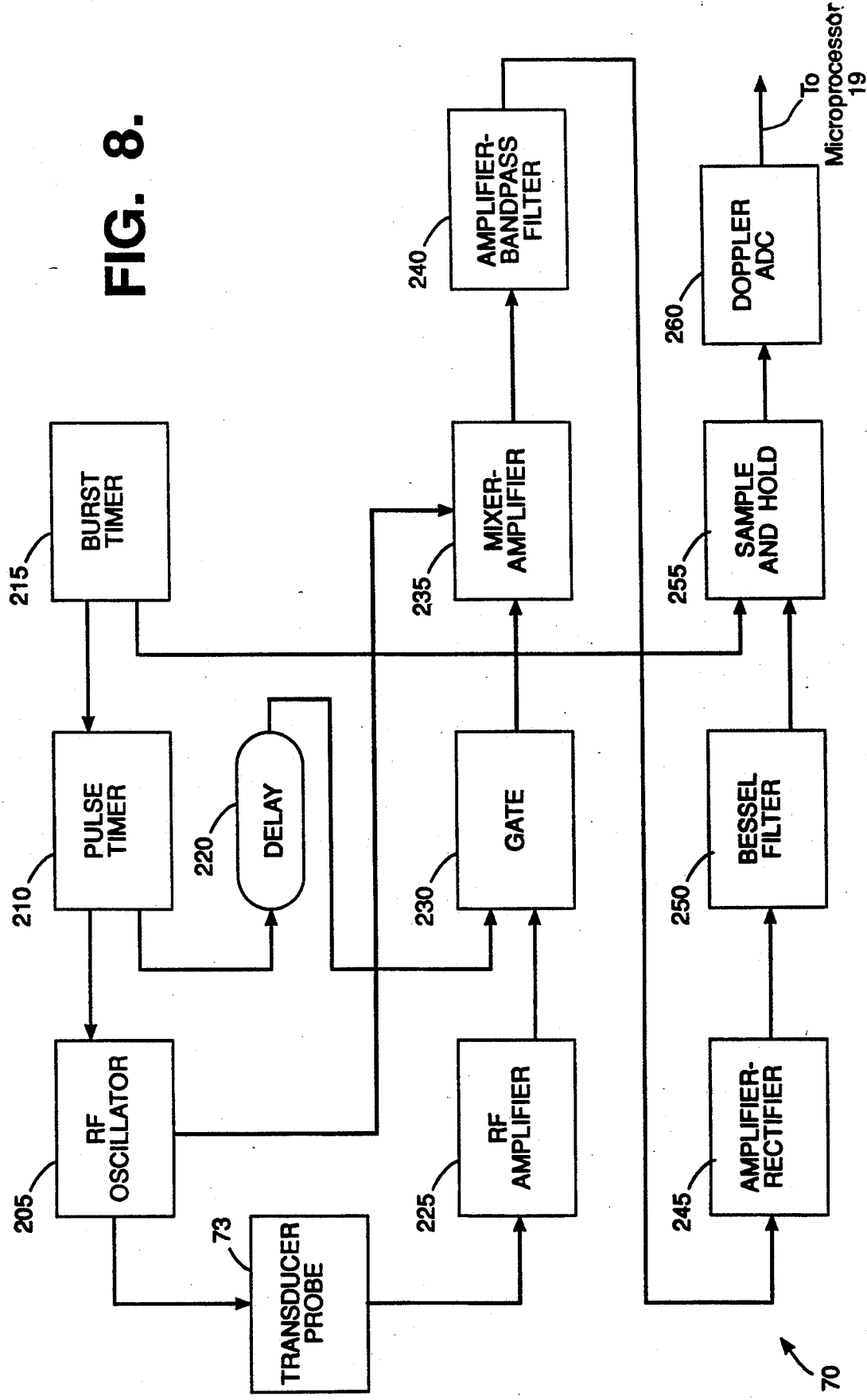

FIG. 16.

```
TCL = 300 ms
V-A = 70% TCL
    = 210 ms
────────────────
A-V = 10 ms
    = 50 ms
    = 100 ms
    = 150 ms
```

TRAIN 1 N=4

| | A-V | | A-V | | A-V | | A-V |
|---|---|---|---|---|---|---|---|
| V-A 210 | | V-A 210 | | V-A 210 | | V-A 210 | |
| | 10 | | 10 | | 10 | | 10 |

TRAIN 2 N=4

| | A-V | | A-V | | A-V | | A-V |
|---|---|---|---|---|---|---|---|
| V-A 210 | | V-A 210 | | V-A 210 | | V-A 210 | |
| | 50 | | 50 | | 50 | | 50 |

TRAIN 3 N=4

| V-A 210 | A-V 100 | V-A 210 | A-V 100 | V-A 210 | A-V 100 | V-A 210 | A-V 100 |
|---|---|---|---|---|---|---|---|

TRAIN 4 N=4

| V-A 210 | A-V 150 | V-A 210 | A-V 150 | V-A 210 | A-V 150 | V-A 210 | A-V 150 |
|---|---|---|---|---|---|---|---|

APPARATUS AND METHOD FOR DETECTING ABNORMAL CARDIAC RHYTHMS USING AN ULTRASOUND SENSOR IN AN ARRHYTHMIA CONTROL SYSTEM

TECHNICAL FIELD

This invention relates to an apparatus and method for detecting abnormal cardiac rhythms and executing antitachycardia pacing (ATP) in an arrhythmia control system. More particularly, the invention relates to implantable medical devices which monitor and control a patient's hemodynamic state by measuring cardiac output from the left ventricle of the heart usihg Doppler ultrasound measurem,ent techniques, storing a history of this cardiac output information over a predetermined period of time, and analyzing this history to detect, classify, and perform a therapy in the form of electrical energy applied to the heart, to revert the abnormal heart rhythms of tachycardia, and fibrillation/flutter and restore the heart's normal sinus rhythm. The invention is described herein as operating in a dual-chamber combined implantable antitachycardia pacing, bradycardia pacing, defibrillating or cardioverting arrhythmia control system. The invention may be incorporated in either a single or dual chamber device performing any one or more of these functions.

BACKGROUND OF THE INVENTION

As used herein, the term tachycardia refers to any fast abnormal rhythm of the heart that is amenable to treatment by electrical discharges and specifically includes supraventricular tachycardia (SVT), atrial tachycardia (AT), atrial fibrillation and atrial flutter (AF), ventricular tachycardia (VT), and ventricular flutter and ventricular fibrillation (VF).

Rubin's U.S. Pat. No. 3,857,398, dated Dec. 31, 1974, and entitled "Electrical Cardiac Defibrillator", describes a combined pacer-defibrillator. This device performs either a bradycardia pacing or a defibrillation function depending on the detection of a VT/VF. If a VT/VF is detected, the device is switched to the defibrillating mode. After a period of time to charge the capacitor, a defibrillation shock is delivered to the patient.

Improvements to this device were contained in a multiprogrammable, telemetric, implantable defibrillator which is disclosed in Gilli et al. copending U.S. Pat. application Ser. No. 239,624, filed Sep. 1, 1988, and entitled "Reconfirmation Prior to Shock in Implantable Defibrillator". The Gilli et al. device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached.

As cardioversion or defibrillation shocks can be very unpleasant to a patient, especially when delivered frequently, it became necessary therefore to provide a device which included antitachycardia pacing therapy along with bradycardia support pacing therapy and defibrillation or cardioversion therapy, so that the implanted device could automatically provide the necessary therapy from a range of therapies offered by the device. Hence a further development in the field of combined implantable devices is described in U.S. Pat. No. 4,940,054, invented by Grevis and Gilli, dated Jul. 10, 1990, and entitled "Apparatus and Method for Controlling Multiple Sensitivities in Arrhythmia Control Systems Including Post Therapy Pacing Delay". This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient.

Additionally, various specific developments have been made in the field of tachycardia control pacers. Tachycardia is a condition in which the heart beats very rapidly, with a ventricular rate higher than 100 beats per minute (bpm) and typically above 150 bpm, and an atrial rate as high as 400 bpm. There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback within the heart. A natural beat results in the feedback of an electrical stimulus which prematurely triggers another beat. By interposing a stimulated heartbeat, the stability of the feedback loop is disrupted.

Langer et al., in U.S. Pat. No. 4,202,340, dated May 13, 1980, and entitled "Method and Apparatus for Monitoring Heart Activity, Detecting Abnormalities, and Cardioverting a Malfunctioning Heart", describes an antitachycardia pacing system which detects VT/VF by deriving a probability density function from the analysis of the amplitudes of intracardiac signals. This antitachycardia pacing system is subject to errors in the delivery of therapy due to the erratic and unpredictable nature of intracardiac signals.

The Langer et al. system disclosed in U.S. Pat. No. 4,475,551, dated Oct. 9, 1984, and entitled "Arrhythmia Detection and Defibrillation System and Method", illustrates arrhythmia detection in which the device first analyzes the probability density function to ascertain abnormal cardiac rhythms such as fibrillation, high rate tachycardias, and low rate tachycardias. Upon the discovery of such rhythms, the device senses heart rate so as to distinguish fibrillation and high rate tachycardia from low rate tachycardia. This device employs a predetermined threshold value for the rate which distinguishes such arrhythmia events.

Geddes' U.S. Pat. No. 4,291,699, dated Sep. 29, 1981, and entitled "Method and Apparatus for Automatically Detecting and Treating Ventricular Fibrillation", characterizes a defibrillator which senses both the electrical and mechanical activity of the heart to detect fibrillation. This device measures the mechanical pumping action of the heart by detecting changes in electrical impedance between a pair of electrodes implanted within one of the ventricles of the heart. The diagnostic relevance of the impedance measurement requires an accurate assessment of electrical conduction volume within the heart. In devices which measure impedance using only two electrodes, gross volume approximation errors occur which lead to large inaccuracies in the impedance measurement. Furthermore, the diagnostic utility of the impedance measurement is degraded by extraneous influences on the impedance signal such as noise from respiration, changes in the patient's posture, and electrical interference.

One recent development in cardiac monitoring and control is the implantable pressure sensor. One example of such control is described in Schroeppel's U.S. Pat. No. 4,708,143, dated Nov. 24, 1987, and entitled "Method for Controlling Pacing of a Heart in Response to Changes in Stroke Volume". Existing cardiac control systems using pressure sensors measure atrial and venous pressures to determine absolute and relative pressure changes during the cardiac cycle, to measure time intervals between electrophysiological phenomena, and to derive an estimate of cardiac output or stroke volume from these measurements. Pressure sensors, even when used in the most effective manner, are implantable only in locations which allow direct measurement of pressure within the right heart, rather than in the left ventricle. Measurements from the right heart poorly estimate the true hemodynamic state of the patient.

It is also known in the art to use noninvasive Doppler ultrasound techniques to measure the maximum blood flow velocity in the aorta or pulmonary artery and to determine cardiac output as a product of the time average mean velocity and the estimated cross-sectional area. One such usage of Doppler ultrasound techniques is described in Colley et al., U.S. Pat. No. 4,319,580, dated Mar. 16, 1982, and entitled "Method for Detecting Air Emboli in the Blood in an Intracorporeal Blood Vessel". Devices use these prior art ultrasound techniques to monitor cardiovascular hemodynamics by measuring cardiac output and stroke volume, but do not use these measurements to control cardiac functions.

Dual chamber heart pacers have been developed in order to generate sequential atrial and ventricular pacing pulses which closely match the physiological requirements of the patient. A conventional dual chamber heart pacer, as disclosed in U.S. Pat. No. 4,429,697 to Nappholz et al. dated Feb. 7, 1984, and entitled "Dual Chamber Heart Pacer With Improved Ventricular Rate Control", includes atrial beat sensing and pulse generating circuits along with ventricular beat sensing and pulse generating circuits. It is known that the detection of a ventricular beat or the generation of a ventricular pacing pulse initiates the timing of an interval known as the V-A delay. If an atrial beat is not sensed prior to expiration of the V-A delay interval, then an atrial pacing pulse is generated. Following the generation of an atrial pacing pulse, or a sensed atrial beat, an interval known as the A-V delay is timed. If a ventricular beat is not sensed prior to the expiration of the A-V delay interval, then a ventricular pacing pulse is generated. With the generation of a ventricular pacing pulse, or the sensing of a ventricular beat, the V-A delay timing starts again. This patent describes how the V-A delay timing interval may be divided into three parts; the atrial refractory period, the Wenckeback timing window, and the P-wave synchrony timing window. It outlines the importance of controlling the ventricular rate in comparison with the atrial rate in order to maintain synchrony between the atrium and the ventricle. The patent does not however address the issue of antitachycardia pacing therapy.

Prior art single chamber antitachycardia pacing devices which provide antitachycardia pacing bursts to either the atrium or the ventricle have shortcomings in that they lack the required synchrony between the atrium and the ventricle. This reduces the percentage of successful reversions, especially in the case of ventricular antitachycardia pacing. Although such pacing may revert an arrhythmia, at the same time however, it increases the risk of adversely affecting the patient by means of a decrease in arterial pressure due to the rapid pacing. Possibly as a result of the hemodynamic compromise or lowered hemodynamic status of the myocardium during the arrhythmia and pacing which reduces electrical conduction in the heart, there is a high risk of a ventricular tachycardia accelerating to a faster ventricular tachycardia and even to a ventricular fibrillation. This has been shown in an article by Fisher et al. entitled "Termination of Ventricular Tachycardia with Burst or Rapid Ventricular Pacing", American Journal of Cardiology, Vol. 41 (January, 1978), page 96. Not only does this present a potentially hazardous situation to the patient, but it also makes it more difficult for the device to revert the patient. Reversion would necessarily demand more energy of the device and perhaps even cardioversion or defibrillation therapy which is not available in many pacing devices. Furthermore, prior art devices are very limited in the provision of individualized therapy to the patient by patient dependent parameters such as the A-V delay.

Many antitachycardia pacing therapy devices at present include defibrillation support within the device in order to provide adequate safety to a patient. It is highly advantageous to prevent the development of VT's or atrial fibrillations, or to terminate them quickly if they appear, rather than allowing the arrhythmia to develop to such an extent that a defibrillation shock is necessary.

The use of antitachycardia pacing therapy in conjunction with a dual chamber pacing device is disclosed in the copending application of Norma L. Gilli, Ser. No. 462,499, filed Jan. 5, 1990, and entitled "Apparatus and Method for Antitachycardia Pacing in Dual Chamber Arrhythmia Control System", which application is assigned to the assignee of the present invention. In the Gilli application upon detection of the presence of a tachycardia, the tachycardia cycle length (TCL) is measured and a V-A interval less than or equal to the TCL is determined, along with an initial value A-V interval. Stimulation pulses are then delivered until the expiration of a given number (N) V-A intervals and N A-V intervals to complete a first train of pulses. A series of a given number (M) of trains of pulses similar to the first train of pulses is delivered, and the A-V delay interval value is varied from the initial value thereof at least once prior to the completion of the series of M trains of pulses. Monitoring of intrinsic QRS complexes between pulse trains is performed. If the tachyarrhythmia is deemed to be accelerating, one of cardioversion or defibrillation is employed. The present invention is an improvement over said Gilli application with respect to the manner of detecting tachyarrhythmias and the manner of setting the A-V interval during the application of antitachycardia pacing therapy.

SUMARY OF THE INVENTION

In accordance with the principles of the present invention, an antitachycardia pacer employs a Doppler ultrasound sensor, implanted within one of the right chambers or the superior vena cava of the heart in a manner such that its interrogation axis is directed toward the vicinity of the left ventricle or aortic root, to assess the heart's cardiac output. This cardiac output measurement provides an exacting criterion for assessing hemodynamic status and enabling precise detection and classification of cardiac arrhythmias and fibrillation. The overriding objective of any hemodynamic control system is to regulate cardiovascular performance and supply the body with a sufficient quantity of oxygenated blood. Therefore, cardiac output, the amount of blood flowing from the heart per unit of time, is the fundamental measurement of interest in implantable cardiac assist devices and the best indicia for determining blood supply adequacy.

An external programmer, supplying appropriate signals to the antitachycardia pacer of the present invention, can enable the pacer to sense cardiac electrical activity in the heart to appraise the instantaneous heart rhythm. The pacer uses heart rhythm measurements in combination with cardiac output measurements to detect and classify abnormal cardiac rhythms into multiple arrhythmia and defibrillation classifications. This pacer generates a sequence of stimulation pulses of predetermined amplitudes, durations, and number to the atria, the ventricles, or both in a programmed antiarrhythmia therapy which the pacer selects according to the detected arrhythmia classification.

In a dual chamber implementation of the antitachycardia pacer of the present invention, the cardiac output measurement is not only the basis for defining and classifying abnormal cardiac rhythms to control an antitachycardia therapy, but is also the control parameter for defining the atrio-ventricular (A-V) delay parameter which maximizes the heart's hemodynamic efficiency.

The Doppler ultrasound transducer is mounted on a catheter which is implanted in the superior vena cava, the high right atrium, or the right ventricle, and is directed towards the ascending aorta, the aortic root, or the aortic arch. Directing the ultrasonic beam in this manner is the best technique for measuring cardiac output to provide for highly accurate detection of changes in the relative amount of blood flowing from the heart's left ventricle. In the preferred embodiment of the invention, a miniature ultrasound transducer is implanted in the superior vena cava, directed so that its sonic axis measures flow in the aortic root. This implantation technique requires only standard electrophysiological procedures. The pacer ensonifies blood with ultrasonic waves, processes returning echoes to extract the audio portion of Doppler ultrasound signals, and analyzes the signals to quantify the cardiac output of the heart. Based on the cardiac output measurement, possibly in combination with rate information generated by pacer sensing and pacing circuitry, the pacer controls an electrical stimulation therapy in a closed-loop feedback control system.

The determination of cardiac output in this manner does not require the estimation of the size of any blood vessels, a difficulty arising in methods known in the art of ultrasonic measurement. The present invention differs from prior art cardiac measurement devices by using Doppler ultrasound techniques to derive an automatic, closed-loop control parameter based on cardiac output to regulate hemodynamic therapy. The closed-loop control parameter allows the device to control an electrical stimulation therapy (i.e., bradycardia pacing, antitachycardia pacing, cardioversion, or defibrillation) by varying one or more of the stimulation timing, frequency, number of pulses in a train, cardiac chamber being stimulated, amplitude, duration, pulse morphology and pattern.

After the transducer radiates ultrasonic acoustic energy, the device determines blood flow velocity by receiving and processing the resulting echoed signals and measuring the shift in frequency of the returning echoes in comparison to the transmitted waves. The integral of the mean velocity curve is an accurate representation of cardiac output.

The objective of prior art noninvasive ultrasound measurement devices is to derive an absolute quantity for the cardiac output, requiring measurement of the cross-sectional area of the blood vessel, measurement and integration of the blood velocity, multiplication of the area and blood volume flow to determine cardiac output or stroke volume, and calibration of the system using measured or estimated coefficients to correlate the results with the results of mroe accurate cardiovascular test methods such as dye indicator techniques. In contrast, the objective of the present invention is to provide a basis for controlling hemodynamics without the necessity of absolute measurements of cardiac output and stroke volume. Therefore, estimation of blood vessel cross-sectional area is not necessary. Relative changes in cardiac output and stroke volume, arising due to changes in the physiological needs of the body and modulated by electrical stimulation or drug therapy, are most valuable for controlling an implantable device.

It is, therefore, an object of the present invention to provide improved detection and classification of abnormal and pathological cardiac rhythms for the purpose of providing improved antitachycardia pacing therapy in an automatic implantable device.

It is a further object of the invention to provide an improved dual chamber ATP device and method which reduce the necessity or the number of defibrillation shocks given to a patient by inhibiting the development of VFs and AFs in the patient through enhanced maintenance of A-V synchony.

It is another object of the invention to provide an improved device and method for distinguishing physiological form pathological cardiac rhythms.

It is yet another object of the invention to individualize the antitachycardia pacing therapy available to each patient in an automatic implantable dual chamber arrhythmia control system by means of automatically optimizing dual chamber pacing parameters, such as the A-V delay, based on an analysis of the patient's cardiac output as detected using Doppler ultrasound techniques.

It is a further object of the present invention to perform ultrasonic analysis to measure cardiac output and control hemodynamic status without invading the left heart or the arterial system of the patient.

In accordance with the principles of one embodiment of the present invention, an antitachycardia pacer and pacing method are provided in which a patient's hemodynamic status is automatically monitored and supported by measuring cardiac output using an ultrasonic sensor. By analyzing cardiac output, a determination is made whether the heart is beating normally (at or near normal rest conditions), or is beating under conditions of stress, exercise, bradycardia, tachycardia, or fibrillation. If the heart is functioning in bradycardia, stress, or exercise, the pacer and method support the patient's hemodynamic status, if necessary, by electrically stimulating the heart. In addition, the pacer analyzes cardiac output information, detects any abnormal rhythms of tachycardia and fibrillation and classifies these rhythms on the basis of this analysis, and initiates an appropriate therapy accordingly.

In accordance with the principles of a second embodiment of the present invention, a rate-responsive dual-chamber antitachycardia pacer and pacing method are provided in which a patient's hemodynamic status is automatically diagnosed and supported by measuring cardiac output using an ultrasonic sensor and sensing intracardiac electrograms to monitor heart rate. By analyzing cardiac output and heart rate information, a determination is made whether the heart is beating normally (at or near normal rest conditions), or is beating under conditions of stress, exercise, bradycardia, tachycardia, or fibrillation. If the heart is functioning in bradycardia, stress, or exercise, the pacer and method support the patient's hemodynamic status, if necessary, by electrically stimulating the ventricle of the heart following an A-V delay interval that is set to maximize cardiac output. The pacer and method periodically perform an A-V delay test procedure to modulate A-V delay interval while performing ultrasonic cardiac output measurements, thereby optimizing the A-V delay parameter. In addition, the pacer analyzes cardiac output and heart rate information, detects any abnormal rhythms of tachycardia and fibrillation and classifies these rhythms on the basis of this analysis, and initiates an appropriate therapy accordingly. The pacer and method perform ultrasonic analysis to measure cardiac output and control hemodynamic status without invading the left heart or the arterial system of the patient.

BRIEF DESCRIPTION OF THE DRAWINGS

Further objects, features and advantages of our invention will become apparent upon consideration of the following description, taken in conjunction with the accompanying drawings, in which:

FIG. 4 is a fragmentary perspective view, with parts cut away for clarity, of one embodiment of the invention, illustrating a pacemaker, a catheter or lead and a Doppler ultrasound sensor shown within the anatomical context of a cardiovascular environment in which the system is implanted;

FIG. 5 is a fragmentary perspective view of the lead shown in FIG. 4;

FIG. 8 is a high-level block diagram of a Doppler signal processor circuit that comprises one of the blocks of FIG. 1;

FIG. 16 illustrates a dual chamber antitachycardia pacing algorithm performed by the preferred embodiment of the invention.

DETAILED DESCRIPTION

Figure 1:
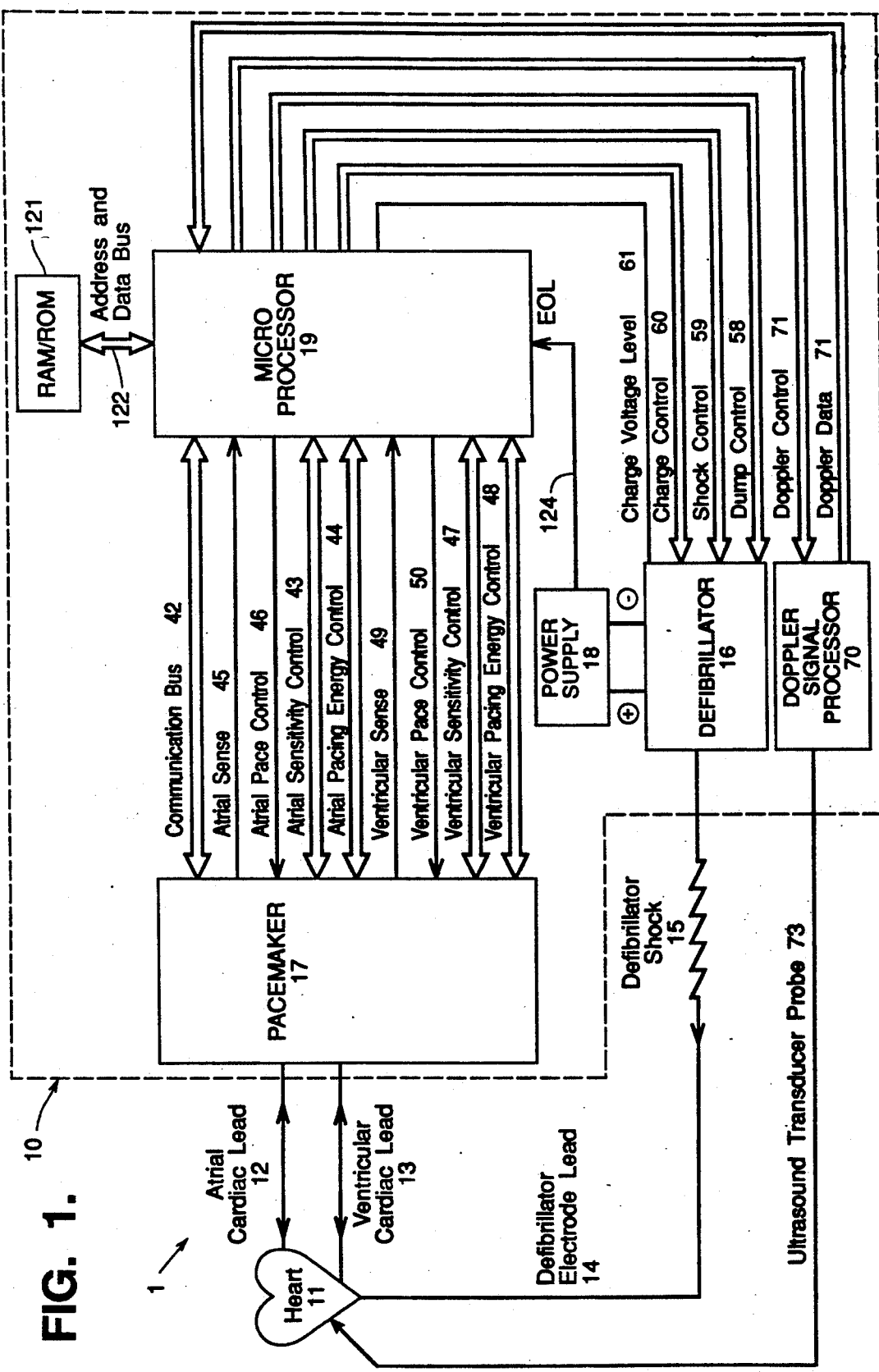
FIG. 1 is a block diagram of an implanted dual chamber arrhythmia control system (ACS) in accordance with the present invention.

Referring to FIG. 1, there is depicted a block diagram of an arrhythmia control system 1. System 1 is designed to be implantable in a patient and includes a cardioverter/defibrillator pacemaker or pulse module 10 and appropriate leads for connecting module 10 to a patient's heart 11. More particularly, system 1 will generally include an atrial cardiac lead 12 extending to the atrium of the patient's heart for the administration of therapy to the atrium, and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16 and a Doppler signal processor 70, performs various operations so as to generate different control and data outputs to pacemaker 17, defibrillator 16 and Doppler signal processor 70; and a power supply 18 for the provision of a reliable voltage level to pacemaker 17, microprocessor 19, defibrillator 16 and Doppler signal processor 70 by suitable electrical conductors (not shown). Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

System 1 performs Doppler signal sensing by activating and sending control signals to Doppler signal processor 70. The microprocessor 19 reads digital Doppler data signals from an output register (not shown) in Doppler signal processor 70 via a Doppler data bus 72. To control Doppler signal acquisition, microprocessor 19 writes control parameters to programmable registers within the Doppler signal processor 70 via a Doppler control bus 71. The Doppler signal processor 70 acquires blood flow information by transmitting signals, via an ultrasound transducer probe 73, into interrogated blood and tissue in bursts of pulsed Doppler acoustic waves. Control information from the microprocessor 19 sets the repetition rate of the bursts (between 20 and 90 Hz), the duration of each Doppler output pulse (between 1.6 and 2.4 usec), the RF oscillator repetition rate, and the depth of the sampling field (by adjusting the delay between transmission and received signal sampling). The microprocessor 19 reads data from the Doppler data bus 72, then sequentially differentiates, integrates, and filters the data signals to construct a Doppler waveform. peak signals in the Doppler Waveform are a manifestation of mechanical events in the cardiac cycle such as the opening and closing of heart valves.

Although the description of the preferred embodiment of the invention expresses the acquisition of Doppler ultrasound waveforms using pulsed Doppler mode, it is within the spirit and scope of the invention to also acquire the waveforms using continuous wave Doppler mode. The pulsed Doppler mode is preferred over continuous wave Doppler mode in a highly compact, implantable system, because the pulsed mode allows for a higher-frequency transducer, requiring an inherently smaller crystal for generating the ultrasonic beam. Additionally, in pulsed Doppler mode, a single crystal acts sequentially as both the transmitter and receiver, avoiding the requirement of a second transducer and thereby reducing the size requirement of the implantable device. Most importantly, pulsed Doppler mode requires less energy than continuous wave Doppler mode. A reduction in energy requirements is highly desirable in a closed-loop pacemaker control system.

Microprocessor 19 is connected to a random access memory/read only memory (RAM/ROM) unit 121 by an address and data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pacing energy control bus 44, a ventricular sense line 49, a ventricular pacing control line 50, a ventricular sensitivity control bus 47, and a ventricular pace energy control bus 48. As also more fully described below, microprocessor 19 is connected to defibrillator 16 by a charge voltage level line 61, a charge control bus 60, a shock control bus 59, and a dump control bus 58.

Figure 2:
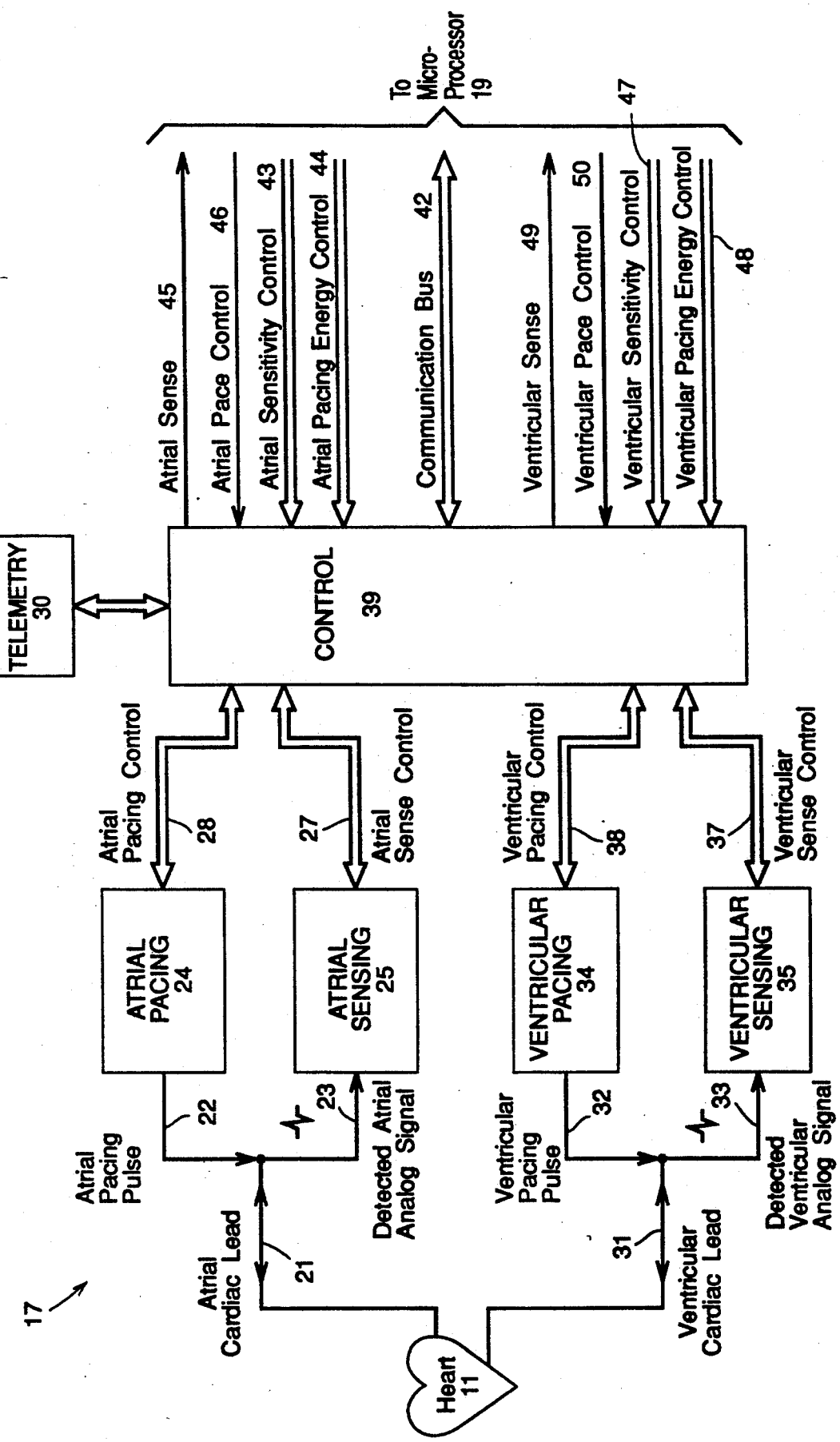
FIG. 2 is a block diagram of a pacemaker utilized in the system of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity affects the voltage deviation required at the sensing electrode for a sense to be registered. The operation of the logic which changes the sensitivity is described in greater detail in the aforesaid U.S. Pat. No. 4,940,054 of Grevis and Gilli, which description is incorporated herein by reference.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in greater detail in U.S. Pat. No. 4,869,252 of Norma Louise Gilli, issued Sep. 26, 1989, and entitled "Apparatus And Method For Controlling Pulse Energy In Antitachyarrhythmia And Bradycardia Pacing Devices," which description is incorporated herein by reference.

Telemetry circuit 30 provides a bidirectional link between control block 39 of pacemaker 17 and an external device such as a programmer. It allows data such as the operating parameters to be read from or altered in the implanted module 10.

Figure 3:
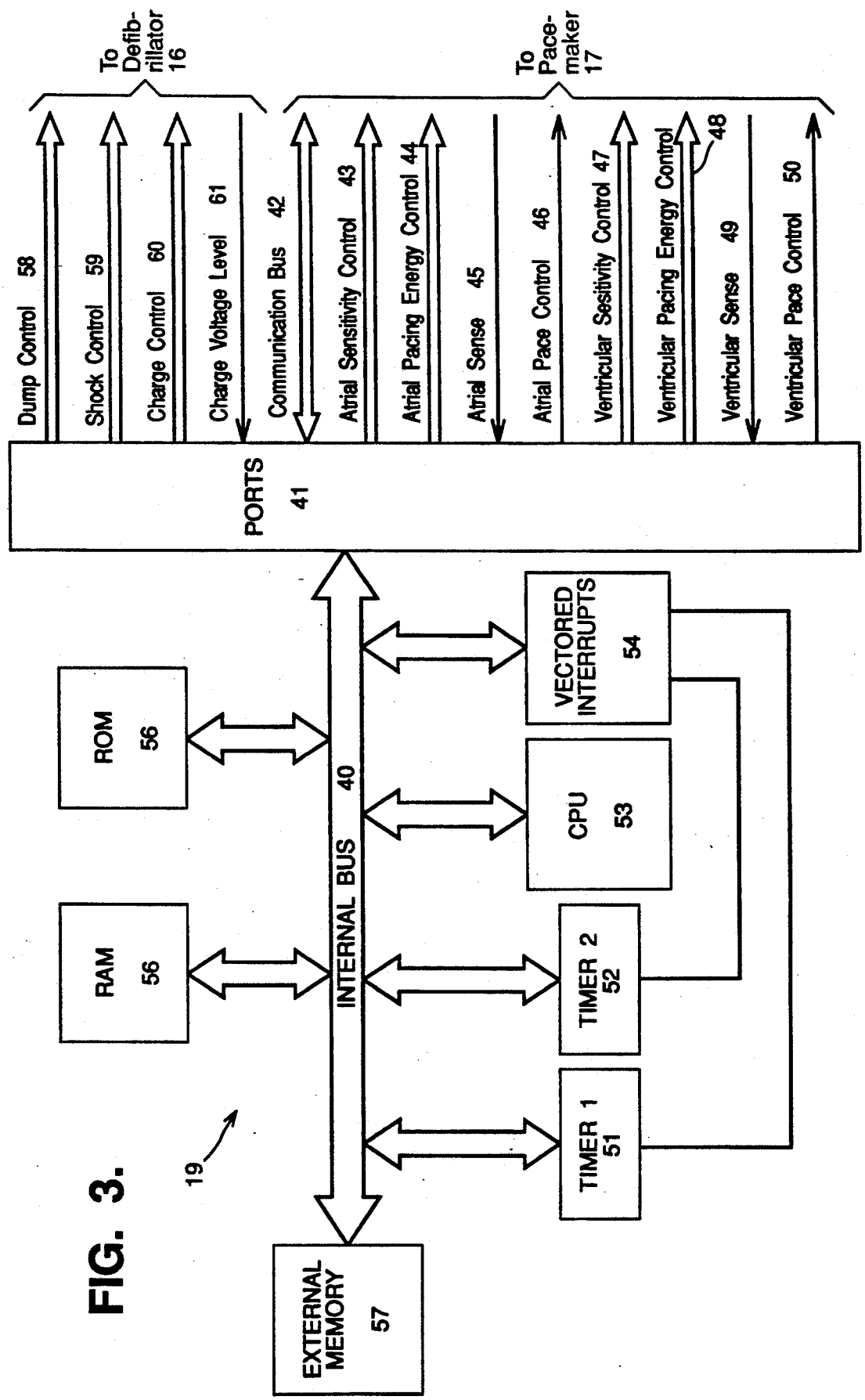
FIG. 3 is a block diagram of a microprocessor utilized in the system of FIG. 1.

Referring to FIG. 3, microprocessor 19 comprises two 16-bit timers 51 and 52, a CPU 53, a vectored interrupts block 54, a ROM 55, a RAM 56, an external memory 57, a ports block 41 and an internal communications bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic flow diagram of FIG. 10, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communications bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communications bus 42, through control block 39 in pacemaker 17, and into telemetry circuit 30 for transmission to the external programmer by a transmitter in telemetry circuit 30.

Microprocessor 19 receives various status and/or control inputs from pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, the shock control on bus 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. Charge voltage level line 61 provides a digital signal representative of charge voltage from an analog-to-digital converter within defibrillator 16, thus providing a feedback loop which assures that a shock of proper energy level is delivered by defibrillator 16.

FIGS. 4 and 5 illustrate a first example of an arrhythmia control system 1 (FIG. 1) having a cardiac assist or therapy device, shown generally at 5A, in the form of a cardioverter/defibrillator pacemaker 10 having an atrial cardiac catheter or lead 12 connecting the pacemaker 10, physically and electrically, to an atrial pacing tip electrode 80. The atrial cardiac lead 12 extends from pacemaker 10 through a patient's cardiovascular system from a vein 81 leading to the superior vena cava 82, through the right atrium 83 and extending into the high right atrium or the atrial appendage 84 of the heart 11, where the atrial pacing tip electrode 80 is implanted. It is known in the art that ultrasonic Doppler probes are capable of longterm viability in an implanted environment.

The atrial pacing tip electrode 80 is implanted into the high right atrium or atrial appendage 84 using an active fixation mechanism such as an atrial lead helical spring 85. An annular piezoelectric ultrasound transducer 86 is affixed to the atrial cardiac lead 12 adjacent to the atrial pacing tip electrode 80. Implantation of the atrial pacing tip electrode 80 is performed in a manner such that the ultrasound beam axis of the annular crystal ultrasound transducer 86 is directed towards and into the ascending aorta 87, allowing the measurement of blood flowing in the ascending aorta 87. Implantation of the catheters and sensors in this manner requires the usage of only conventional catheter-based right heart techniques. From this measurement of flow, the device 5A derives a measurement of cardiac output at the aortic root 88. The ability to measure the cardiac output at the aortic root using Doppler ultrasound is important because it enables the implementation of a fully closed-loop cardiac system for monitoring and controlling blood flow. Automatic control of metabolic demand and hemodynamic status is possible only if cardiac output at the aortic root is known.

FIG. 5 shows the atrial cardiac lead portion 12 of device 5A in greater detail and illustrates the arrangement of annular piezoelectric ultrasound transducer 86 relative to the lead 12, a pacing ring electrode 89, atrial pacing tip electrode 80 and atrial lead helical spring 85. An active fixation device, such as atrial lead helical spring 85, is normally affixed to atrial tissue when an appropriate activating member or stylet (not shown), which may be passed through lumen 150 of an inner insulating tube 151, engages a slot 152 in a rotationally supported driving member 153, and is rotated, as is well known in the art. Two wire coil conductors 62 and 63, which are separated by an intermediate insulating tube 154, extend longitudinally within tube 151 to connect atrial pacing ring electrode 89 and atrial pacing tip electrode 80, respectively, with a suitable connector (not shown) to pacemaker module 10. The annular piezoelectric ultrasound transducer 86 transmits and receives, through an epoxy window 76, ultrasonic energy generated by an annular ultrasound crystal 75, which is affixed to an epoxy base containing hollow glass spheres 77. Epoxy window 76 may be composed of polyethelene or parazylene. Hollow glass spheres 77 provide a dampening effect on the received ultrasound energy. Ultrasound crystal 75 is electrically connected with ultrasound signal processing circuitry (not shown in this figure) within system 1 by means of a micro-coaxial cable 78.

Figure 7:
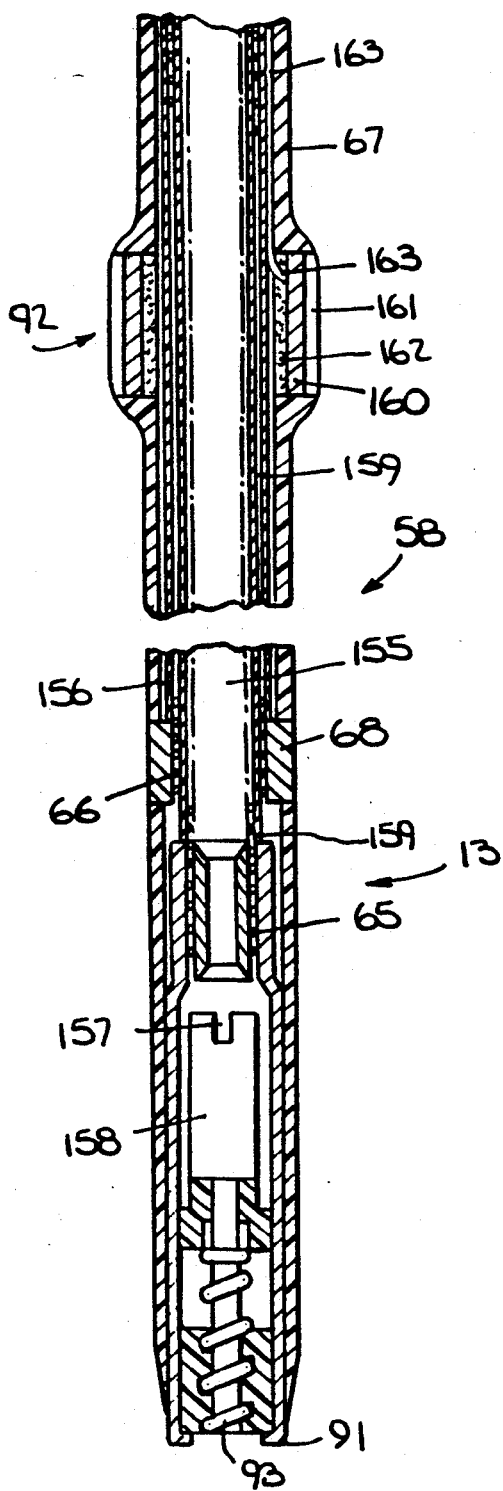
FIG. 7 is a fragmentary perspective view of the lead shown in FIG. 6.
Figure 6:
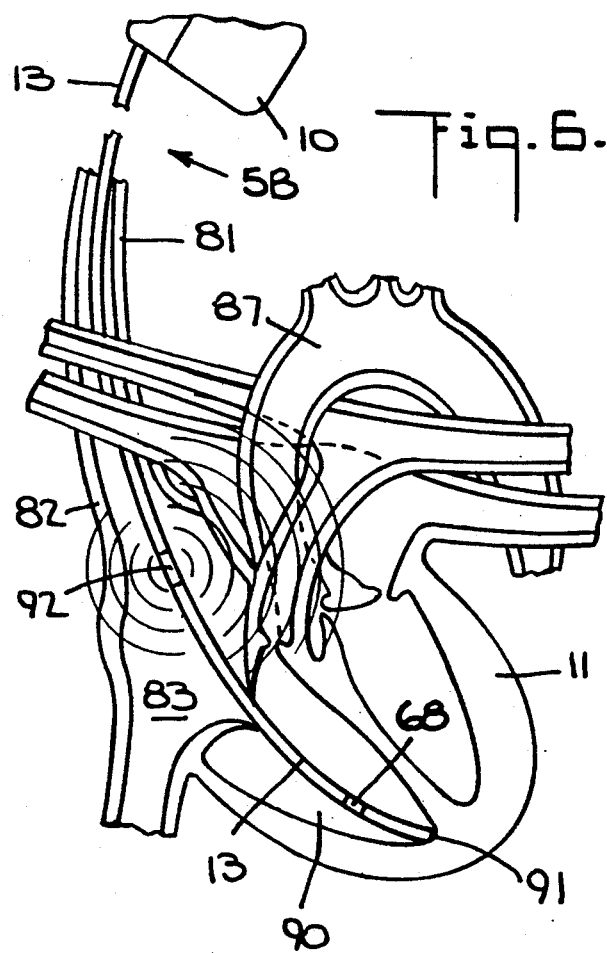
FIG. 6 is a fragmentary perspective view, with parts cut away for clarity, of a second embodiment of the invention, illustrating the pacemaker, the lead and the Doppler ultrasound sensor shown within the anatomical context of a cardiovascular environment in which the system is implanted.

FIGS. 6 and 7 illustrate a second example of an arrhythmia control system 1 (FIG. 1) having a cardiac assist or therapy device, shown generally at 5B, in the form of a cardioverter/defibrillator pacemaker 10 having a ventricular cardiac catheter or lead 13 connecting the pacemaker 10, physically and electrically, to a ventricular pacing tip electrode 91. The ventricular cardiac lead 13 extends from pacemaker 10 through a patient's cardiovascular system from a vein 81 leading to the superior vena cava 82, through the right atrium 83 and then into the right ventricle 90 of the heart 11, where the ventricular pacing tip electrode 91 is implanted.

The ventricular pacing tip electrode 91 is implanted into the apex of the right ventricle 90 using standard electrophysiology techniques in which an active fixation mechanism such as a ventricular lead screw 93 affixes the electrode to the cardiac tissue. At an appropriate location on the ventricular cardiac lead 13, a cylindrical piezoelectric ultrasound transducer 92, having the form of a tube or ring, encircles and joins electrically with the ventricular cardiac lead 13. Implantation of the ventricular pacing tip electrode 91 is performed in a manner such that the cylindrical piezoelectric transducer 92 is situated within the superior vena cava 82 or high right atrium 83. Pacemaker 10 electrically excites the ultrasound transducer 92, causing the piezoelectric elements of the transducer to emit ultrasound waves which extend in all directions perpendicular to the surface of the cylindrical transducer 92. The emitted ultrasonic waves interrogate the blood and tissue in nearly a spherical pattern. Since the ascending aorta 87 characteristically has the largest blood volume and highest blood flow velocity within the detection range of the transducer, the ultrasound signals having the greatest amplitude returning to the transducer 92 predominantly reflect the influence of blood flow within the ascending aorta. Signals returning from other blood vessels are attenuated by intervening tissue and have a much lower amplitude. The pacemaker 10 control circuitry classifies these extraneous signals as background noise.

FIG. 7 shows the ventricular cardiac lead portion 13 of device 5B in greater detail and illustrates the arrangement of cylindrical piezoelectric ultrasound transducer 92, showing its position relative to the ventricular cardiac lead 13, a pacing ring electrode 68, pacing tip electrode 91 and ventricular lead helical spring 93. An active fixation device, such as ventricular lead helical spring 93, is normally affixed to tissue when an appropriate activating member or stylet (not shown), which may be passed through lumen 155 of lead 13, engages a slot 157 in a rotationally supported drive member 158, and is rotated. Two wire coil conductors 66 and 65, which are separated by an intermediate insulating tube 159, extend longitudinally within lead 13 to connect ventricular pacing ring electrode 68 and ventricular pacing tip electrode 91, respectively, with a suitable connector (not shown) to pacemaker module 10. The cylindrical piezoelectric ultrasound transducer 92 includes a cylindrical crystal 160, positioned between an epoxy window 161 on the exterior and an epoxy substrate 162. The epoxy substrate 162 is filled with hollow glass spheres to dampen the received ultrasonic energy. The cylindrical crystal 160 is electrically connected with ultrasound signal processing circuitry (not shown in this figure) within the system 1 by means of a microcoaxial cable 163 which is interposed between an insulating tube 156 that surrounds coil 66 and an exterior silastic sheath 67. When ventricular pacing tip electrode 91 is implanted in the apex of the right ventricle 90, the length of the portion of the lead extending from the pacing tip electrode 91 to the cylindrical piezoelectric ultrasound transducer 92 is selected to place the transducer either within the superior vena cava 82 or the high right atrium 83 of FIG. 6, according to the desires of the surgeon. In this manner, a surgeon implants the catheters and sensors using conventional catheter-based right heart techniques.

Referring now to FIG. 8, the Doppler signal processor 70 includes a burst timer 215 for producing timing signals at a programmed burst repetition rate ranging in frequency from 20 to 90 Hz. By acquiring pulsed Doppler waveforms in a burst mode, the device further reduces energy expenditure by transmitting acoustic waves only part of the time. The repetition rate must be sufficient to preserve the informational content of the left ventricular output (the pulsatile frequency of which ranges from 1 to 6 Hz) and is controlled by means of control signals from the microprocessor 19 (FIG. 1) which set the frequency of a Doppler RF oscillator 205. One millisecond duration pulses from the burst timer 215 trigger the activation of a pulse timer 210 which, in turn, produces pulses of a programmable duration (1.6 to 2.4 usec), timing control signals which extend to the RF oscillator 205 and extend to a delay circuit 220. The RF oscillator 205 produces a 7 MHz electrical signal, in the form of a sinusoidal burst of 8 to 12 cycles at a programmable repetition rate of 33 to 100 kHz every 11 to 50 msec, and sends the signal to a Doppler ultrasound transducer or probe 73 (e.g. transducer 86 of FIG. 5 or transducer 92 of FIG. 7) over the transmitter connection of a micro-coaxial cable (e.g., cable 78 of FIG. 5 or cable 163 of FIG. 7). The RF oscillator 205 outputs 2 volts RMS into a 50 ohm load. The RF oscillator also provides a 600 mv RMS electrical signal to a mixer/amplifier 235.

The Doppler ultrasound transducer probe 73 converts the signal from the RF oscillator 205 into an acoustical waveform which it emits into the body for the purpose of acoustic interrogation. The Doppler ultrasound transducer probe 73 receives returning echoes from the blood and tissue and converts the returning acoustical waveforms into electrical signals. The receiver connection of the aforesaid microcoaxial cable passes these signals to an RF amplifier 225. The RF amplifier has a gain of about 1000 to amplify the 0.2 to 20 microvolt signals from the Doppler ultrasound transducer into millivolt level RMS signals which are input into a gate circuit 230. The RF amplifier 225 performs bandpass filtering to produce a waveform with frequency components in the range of from 200 kHz to 8 MHz. The gate circuit 230 performs range gating of the electrical signal processed from the echoes received by the Doppler ultrasound transducer probe 73. By performing range gating, the Doppler system can measure blood flow information at a particular depth from the transducer rather than detecting information averaged over the entire penetration depth. A control register in the gate circuitry 230, for selecting duration, is programmable in the range of from ten to thirty microseconds to provide for adjustment of the depth of the sampled field. The gate circuit 230 has unity gain and performs bandpass filtering from 100 kHz to 14 MHz.

Timing signals from the delay circuit 220 determine the depth of the ultrasound field of view. The delay circuit 220 performs timing for the purpose of range gating and has a programmable delay of from 15 to 35 usec. The delay circuit 220 and the gate circuit 230 act in concert to determine the measurement range of the Doppler system. The delay circuit sets the distance from the Doppler ultrasound transducer probe 73 to the start of the field of view at which the system begins sampling. The gate circuit 230 sets the depth or range of the field of view sampled, from the most proximal to the most distal depth of the interrogated blood and tissue. The depth of the actual field of view sampled depends on parameters including the programmed delay and gate values, frequency characteristics of the ultrasound transducer and the speed of sound in the body. When interrogating the ascending aorta from a transducer located in the superior vena cava, the field of view is programmed to sample a depth range of from 3 to 5 cm.

Gated signals from the gate circuit 230 pass to the mixer/amplifier 235 which compares the frequency information of the interrogating and echoed signals to determine velocity within the ultrasound field. The function of determining velocity from acoustic signals as performed by the mixer/amplifier 235 is standard in the art of Doppler measurement devices. An amplifier/bandpass filter 240 is the combination of an audio amplifier (with an audio frequency bandwidth of 370 to 7600 Hz and a gain of 500) and a two pole bandpass filter (with a Q of 1, an adjustable center frequency between 1 and 3 kHz and a midband gain of 2.67). The amplifier/bandpass filter 240 elevates the amplitude of the signal at the mixer/amplifier 235 output from the level of a few millivolts to the range of about one volt. This operation is the first stage in the process of converting the spectral components of the audio signal arising from the mixer/amplifier 235 to a continuously varying voltage.

The output of the amplifier/bandpass filter 240 is an amplitude modulated signal, which is led to an amplifier/rectifier 245. The purpose of amplifier/rectifier 245 is to remove the radio frequency components of the amplitude modulated signal. The first stage of amplifier/rectifier 245 is an amplifier with a fixed gain of 51 and a bandwidth from 10 Hz to 16 kHz. This first stage boosts the signal amplitude and removes high frequency noise resulting from a differentiation operation in the amplifier bandpass filter 240. The final stage of amplifier/rectifier 245 is a full wave, unity gain, precision rectifier with a dynamic range of 30 dB which passes signal frequencies from DC to 10 kHz.

A three pole, unity gain, 6 Hz Bessel filter 250 removes the audio frequency signal components out of the amplitude modulated output of the amplifier/rectifier 245. A sample and hold circuit 255 samples the output of the Bessel filter 250 in preparation for conversion to digital form by a Doppler analog to digital converter (ADC) 260. The digital output of the Doppler ADC 260 is sent to microprocessor 19 (FIG. 1) and is used to determine cardiac output, or to measure pulse wave parameters in the peripheral vascular system, depending on the type of device 5A, 5B (FIGS. 5,7) utilized.

Figure 9:
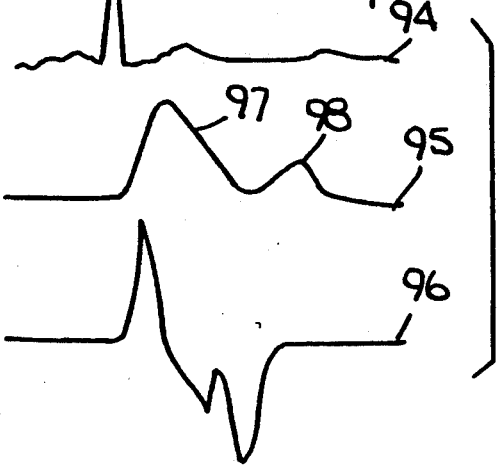
FIG. 9 comprises a series of graphical representations along a time axis of an intracardiac electrogram, a Doppler waveform and a differentiated Doppler signal, showing a correspondence in timing between the various signals.

FIG. 9 comprises an example of graphical representations along a time axis of an intracardiac electrogram 94, a Doppler waveform 95 and a differentiated Doppler signal 96. It shows the correspondence in time between the blood flow as represented by pulsed Doppler signal 95, the velocity of blood flow displayed by differentiated pulsed Doppler signal 96, and the heart's electrical activity shown by intracardiac electrogram 94. These waveforms are indicative of the amplitude and timing of signals that could be sensed and measured by the system of the present invention. Doppler E wave 97 indicates the relative magnitude of the cardiac output, i.e., the amount of blood flowing from the ventricle. Doppler A wave 98 follows the Doppler E wave 97. The Doppler A wave 98 is indicative of the amount of atrial filling. The microprocessor 19 of FIG. 1, samples the output from the input/output register (DOPP) of the Doppler ADC (260) upon data conversion. Upon sampling the DOPP data, the microprocessor 19 integrates the data for the duration of a cardiac cycle, as determined by standard sensing and pacing operations, to determine the cardiac output value for the current cycle. The microprocessor 19 derives a running average of these cardiac output values using standard digital filtering techniques. The time constant of the digital filter ranges from one to four hours.

The primary function of the antitachycardia pacer module 10 (FIG. 1) is the detection and classification of cardiac arrhythmias and, in response to such an arrhythmia, the initiation and automatic control of an appropriate therapy. An arrhythmia detector in module 10 analyzes either cardiac output measurements alone, or cardiac output measurements in conjunction with cardiac rhythms sensed from cardiac electrical signals, to detect arrhythmias. This analysis requires comparison with standard levels of cardiac output or cardiac output and heart rate. Prior to enabling the antitachycardia detection function, a physician must perform electrophysiology tests for a particular patient to establish these standards.

During electrophysiology testing, a physician determines cardiac output or cardiac output and rhythm limits which define different classifications and types of arrhythmias. The cardiac output limits are in the form of a percentage reduction from a continuously averaged cardiac output norm. The rhythm limits are absolute heart rate boundaries, called tachycardia cycle length (TCL) limits. In addition to setting these limits, the physician prescribes a therapy for each of a plurality of arrhythmias.

Figure 10:
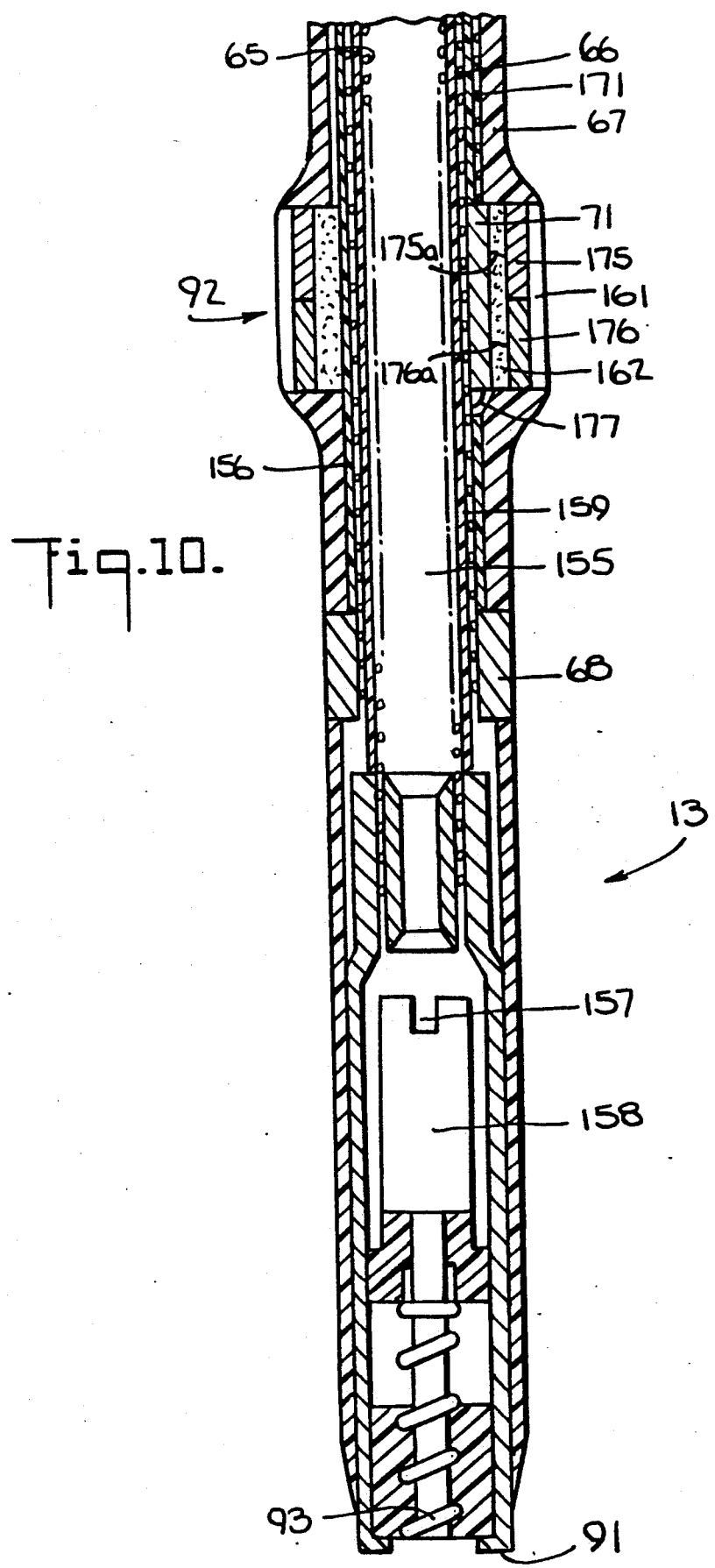
FIG. 10 is a fragmentary perspective view of an additional embodiment of the lead shown in FIG. 7.

FIG. 10 shows an additional embodiment of the ventricular cardiac lead portion 13 of device 5B which was previously illustrated in FIG. 7. The FIG. 10 embodiment includes a probe IC or miniature integrated circuit 71, which performs high frequency signal processing of ultrasound signals. The following elements are identical in form and function in both the FIG. 7 embodiment and the FIG. 10 embodiment of the invention: the pacemaker 10, coil conductors 65 and 66, the silastic sheath 67, the pacing ring electrode 68, the pacing tip electrode 91, the cylindrical piezoelectric ultrasound transducer 92, the ventricular lead helical spring 93, the lumen 155, the outer insulating tube 156, the slot 157 in driving member 158, intermediate insulating tube 159, the epoxy window 161, the interior epoxy substrate 162.

In FIG. 10, the probe IC 71 is electrically interconnected with a cylindrical ultrasound transmission crystal 175 and a cylindrical ultrasound receiving crystal 176 by respective pairs of conductors represented diagrammatically at 175a and 176a. It is mounted on the outer coil 66 within the ultrasound transducer 92 and processes the high frequency ultrasound signals into low frequency data, obviating the need for the micro-coaxial cable 163 (FIG. 7) to carry high frequency signals to the pacemaker 10. Replacing the micro-coaxial cable 163 of FIG. 7 with two wires, Iout 177 and Vsupply 171 of FIG. 10, conserves energy losses along the cable and precludes breakage of the cable caused by long-term flexion of the catheter, which is common in an implantable system.

Vsupply 171 may be a third wire coil that is interposed between the insulating tube 156 and the exterior silastic sheath 67. To reduce the number of wires within the catheter, thereby reducing the likelihood of wire breakage, Iout 177 is electrically connected to the wire coil conductor 66 which interconnects the pacing ring electrode 68 and the pacemaker 10.

Figure 11:
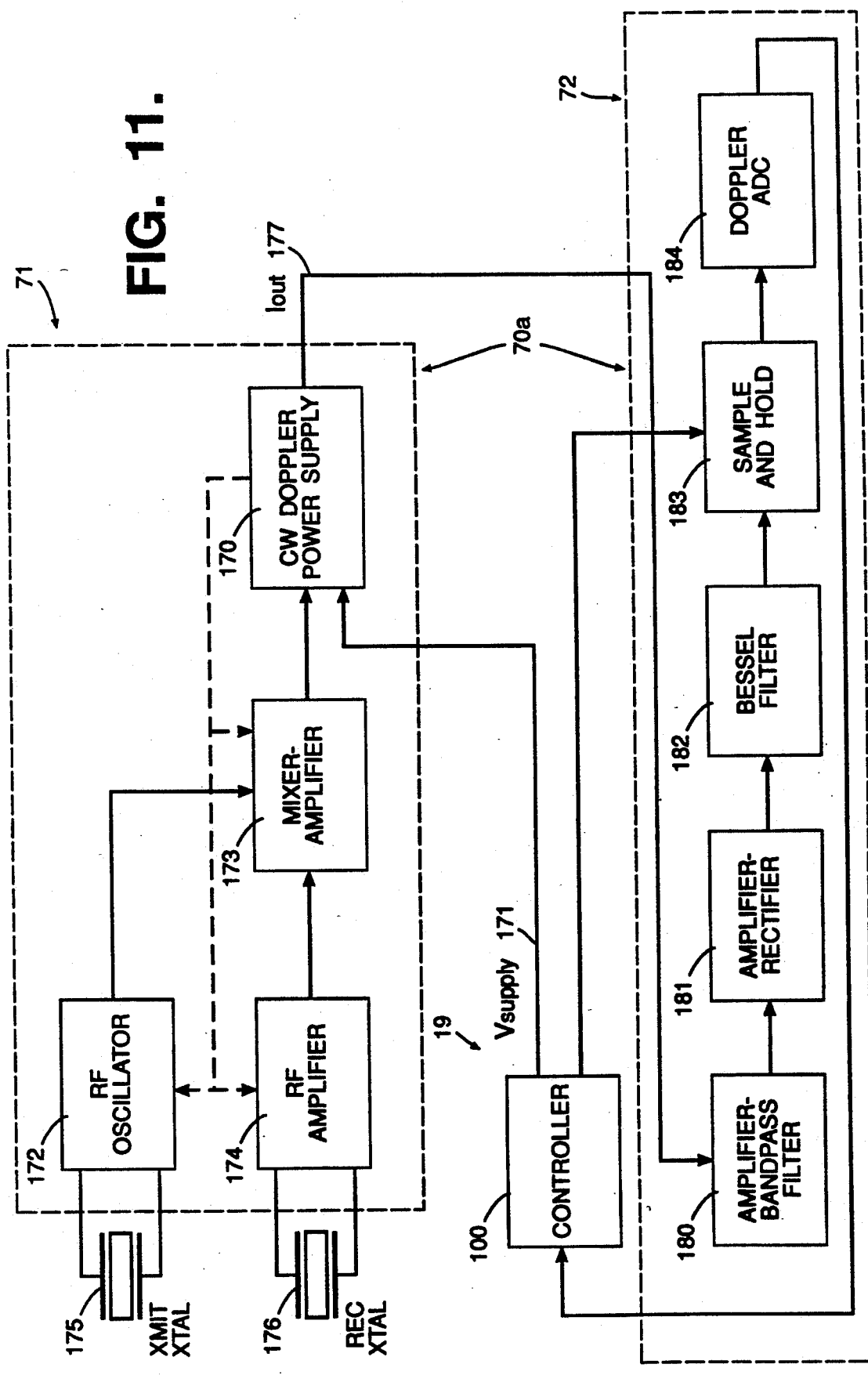
FIG. 11 is a high-level block diagram of a Doppler signal processor circuit that comprises one of the blocks of FIG. 8, in which part of the circuit is located within the lead shown in FIG. 10.

FIG. 11 illustrates a high level block diagram of an embodiment 70a of the Doppler signal processor 70 of FIGS. 1 and 8 that may be used with the cardiac lead 13 shown in FIG. 10. This processor implements ultrasound measurements in a COntinuous wave, rather than employing a pulsed mode of operation. A controller 100, within microprocessor 19, commands continuous wave Doppler signal processor 70a by controlling the delivery of voltage on Vsupply line 171 to CW Doppler power supply 170. Controller 100 performs software routines which determine when to sample blood flow signals. These software routines act as a burst timer to synchronize blood flow sampling with the heart's electrical events. For example, controller 100 detects a QRS-complex within the intracardiac electrogram, waits for a predetermined interval (e.g., 150 ms), then measures blood flow by sampling Doppler signals for another predetermined time (e.g., 100 ms). The controller may measure blood flow on every cardiac cycle, or may sample only occasionally (e.g., every 4 seconds) to conserve energy.

In addition, controller 100 may control the measurement of other physiological parameters which may influence the blood flow measurement. For example, respiration by the patient generates an artifact in the blood flow measurement which may reduce the effectiveness of control methods based on blood flow. A pacemaker may include respiration sensing to control pacing rate, as is disclosed by Nappholz et al. in U.S. Pat. No. 4,901,725, dated Feb. 20, 1990, and entitled "Minute Volume Rate-Responsive Pacemaker". In a system which combines minute ventilation sensing with Doppler ultrasound blood flow measurements, the controller can synchronize the blood flow measurement with respiration (either inspiration or expiration) and with position within the cardiac cycle. In general, the best ultrasound sensing occurs during the expiration portion of the respiratory cycle.

The Doppler signal processor 70a of this embodiment is comprised of circuits which include an ultrasound probe integrated circuit (probe IC 71) and an ultrasound signal processor 72. The probe IC 71, which corresponds to probe IC of FIG. 10, is connected to a pair of ceramic crystals 175 and 176 which are mounted near the distal end of a chronic pacing catheter. The probe IC 71 comprises high frequency signal processor circuitry including the CW Doppler power supply 170, an RF oscillator 172, a mixer-amplifier 173, and an RF amplifier 174, all of which are mounted on the catheter within a few millimeters of the ceramic crystals. The ultrasound signal processor 72 is located within the pacemaker case, rather than on the catheter, and communicates with the proce IC electronics by way of two wire coils, Vsupply line 171 and a current output line, Iout 177 (which includes coil 66). The ultrasound signal processor 72 is comprised of an amplifier-bandpass filter 180, an amplifier-rectifier 181, a Bessel filter 182, a sample and hold circuit 183, and a Doppler analog to digital converter 184.

When the controller 100 applies voltage on Vsupply line 171, the CW Doppler power supply 170, in turn, provides operating energy to RF oscillator 172, a mixer-amplifier 173, and RF amplifier 174. Upon activation, the RF oscillator 172 generates and applies a continuous sinusoidal 8 MHz electrical signal to transmission crystal 175 (e.g., in transducer 92 of FIG. 6, 7 and 10). In the preferred embodiment of the invention, the transmission crystal CW power is about 50 uW in 50 ohms. In addition to exciting the transmission crystal, the RF oscillator 172 also provides a 600 mv RMS electrical signal to a mixeramplifier 173. The transmission crystal 175 acts as a tuning element for RF oscillator 172. This allows tracking between the RF oscillator 172 and the mixer-amplifier 173 oscillator as the transmission crystal 175 absorbs fluids which, in turn, causes a shift in the resonant frequency of the crystal.

The transmission crystal 175 converts a signal from the RF oscillator 172 into an acoustical waveform which it emits into the body for the purpose of acoustic interrogation. The receiver crystal 176 receives returning echoes from the blood and tissue, converts the returning acoustical waveforms into electrical signals, and passes these signals to the RF amplifier 174. The RF amplifier has a gain of about 1000 to amplify the 0.2 to 20 microvolt signals from the Doppler ultrasound transducer into millivolt level RMS signals which are input into the mixer-amplifier 173. The RF amplifier 174 augments the signal from the receiver crystal 176 by a first stage receiver RF gain of at least ten to eliminate voltage noise from subsequent filtering and amplification stages.

The mixer-amplifier 173 compares the frequency information of the interrogating and echoed signals to determine velocity within the ultrasound field. The function of determining velocity from acoustic signals as performed by the mixer-amplifier 173 is standard in the art of Doppler measurement devices.

The output signal of the mixer-amplifier 173 is a baseband audio signal which is input to the CW Doppler power supply 170 for the purpose of modulating the power supply load current, Iout 177. Blood flow information is sent from the CW Doppler power supply 170 to the amplifier-bandpass filter 180 circuit using current loop communication in which the baseband audio signal from mixer-amplifier 173 modulates Iout 177. The CW Doppler power supply 170 circuit includes a capacitor which filters the ultrasound frequency signals within the probe IC 71, while retaining and transmitting on Iout 177 the signal variations in the baseband audio load. In this manner, the control commands into the probe IC and output signals representing blood flow are communicated between the pacemaker and the catheter tip by means of two wires, rather than a pair of microcoaxial cables. In an implantable system, elimination of a coaxial cable is desirable because the cable is subject to large power losses and is not sufficiently durable to withstand the large number of flexures common for a pacing catheter.

Within the ultrasound signal processor 72, the amplifier-bandpass filter 180 is a combination of an audio amplifier (with an audio frequency bandwidth of 370 to 7600 Hz and a gain of 500), a nine pole switched capacitor filter and a two pole bandpass filter (with a Q of 1, an adjustable center frequency between 1 and 3 kHz and a midband gain of 2.67). The amplifier-bandpass filter 180 elevates the amplitude of the signal at the mixer-amplifier 173 output from the level of a few millivolts to the range of about one volt. This operation is the first stage in the process of converting the spectral components of the audio signal arising from the mixer-amplifier 173 to a continuously varying voltage.

The output of the amplifier-bandpass filter 180 is an amplitude modulated signal, which is input to amplifier-rectifier 181. The amplifier-rectifier 181 removes phase variations from the amplitude modulated signal. The first stage of amplifier/rectifier 181 is an amplifier with a fixed gain of 51 and a bandwidth from 10 Hz to 16 kHz. This first state raises the signal amplitude and removes high frequency noise resulting from a differentiation operation in the amplifier-bandpass filter 180. The final stage of amplifier-rectifier 181 is a full wave, unity gain, precision rectifier with a dynamic range of 30 dB which passes signal frequencies from DC to 10 kHz.

A three pole, unity gain, 6 Hz Bessel filter 182 removes the audio frequency signal components out of the amplitude modulated output of the amplifier-rectifier 181. A sample and hold circuit 183 samples the output of the Bessel filter 182 in preparation for conversion to digital form by a Doppler analog to digital converter (ADC) 184. The digital output of the Doppler ADC 184 is sent to controller 100 and is used to determine cardiac output or to measure pulse wave parameters in the peripheral vascular system.

Figure 12:
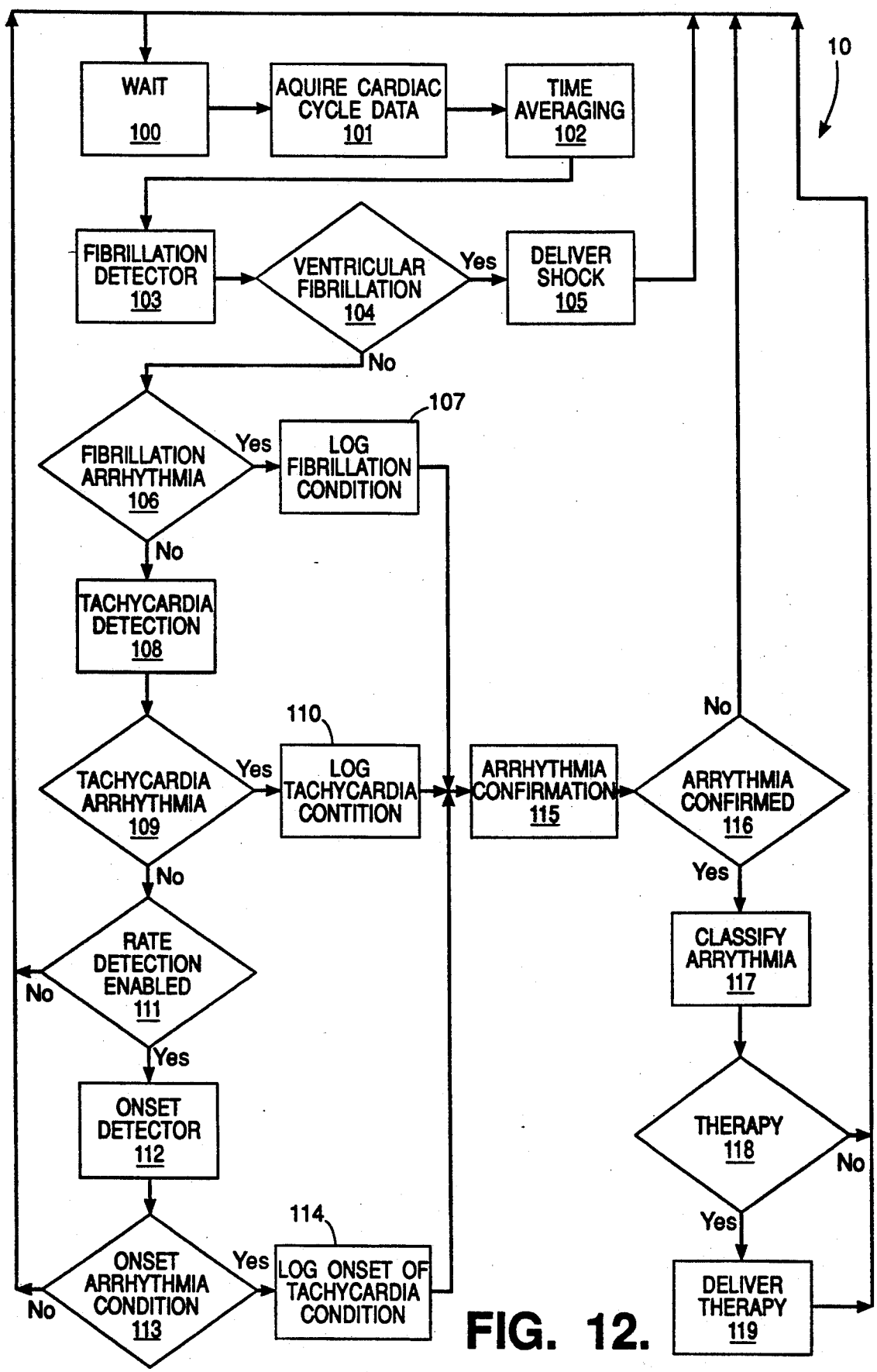
FIG. 12 is a flow chart illustrating the operational steps of an arrhythmia detection/classification function performed by the illustrative embodiments of the invention.

Referring to FIG. 12, which is a flow chart illustrating the operational steps of an arrhythmia detection/classification function performed in pacemaker module 10, starting from a wait state in block 100 an arrhythmia detector and classifier portion of the pacer 10 first acquires cardiac cycle data in block 101. This data includes a cardiac output measurement from the current cardiac cycle and, if selected, heart rate information. The pacer 10 measures heart rate using internal timers. Timer circuits and heart rate data processing are common in pacemakers.

After acquiring the cardiac output data, the pacer 10 performs time averaging in block 102 to update a cardiac output value for the normal, resting heart. Time averaging includes short term and long term averaging of the cardiac output parameter. Averaging eliminates non-diagnostic changes in cardiac output arising from day to day and circadian rhythm variability, as well as randomness arising from external influences such as drug therapy. The pacer addresses both short term and long term variability problems by averaging the cardiac output data using lowpass filtering techniques.

For each cardiac output measurement within the aforementioned limits, the pacer lowpass filters the data on a short term basis to provide an averaged characterization of cardiac output over roughly the last fifteen seconds or less (called "COavg") and further lowpass filters the data on a long term basis to designate the standard level of cardiac output (called "COstd") for about a four hour period. The pacer performs short term average filtering and long term average filtering in time averaging block 102, using recursive filtering techniques which are well-known in the art of signal processing. The short term filter memory, called the cardiac output average (COavg), is described by the following equation, in which "COavg$_i$" represents the current value of a short term filter accumulator, COavg$_{i-1}$ represents the value of the short term filter accumulator at the end of the next previous cardiac cycle and "COcycl$_i$" is the cardiac output sample value for the current cardiac cycle:

$$COavg_i = 63/64 \times COavg_{i-1} + COcycl_i.$$

The long term filter memory, called the cardiac output standard (COstd), is described by the following equation, in which "COstd$_i$" represents the current value of a long term filter accumulator, "COstd$_{i-1}$" represents the value of the long term filter accumulator at the end of the next previous cardiac cycle and "COavg$_i$" is the current value of cardiac output short term average:

$$COstd_i = 127/128 \times COstd_{i-1} + COavg_i.$$

After performing short and long term average filtering in block 102, the pacer 10 analyzes cardiac output or combined cardiac output and heart rate data in arrhythmia detection analysis blocks 103, 108 and 112 for the purpose of detecting cardiac arrhythmias. The pacer compares the short term average cardiac output, COavg, to the long term average cardiac output standard, COstd. The pacer may use this cardiac output information in combination with heart rate data to perform preliminary detection of arrhythmias.

An optional heart rate data evaluation arrangement for the arrhythmia detection analysis blocks 103, 108 and 112 uses the timing of sensed or paced cardiac events to update an X out of Y detector (X/Y detector). In this arrangment the pacer measures time intervals between successive cardiac events for each cardiac cycle, compares each interval to a predetermined standard, and inserts the result of this comparison into a memory containing a history of such results. The X/Y detector analyzes this history according to a preset detection criterion, X out of Y (for example, 8 out of 10 intervals). The cardiac rhythm meets this detection criterion when at least X of the Y most recent intervals are shorter than, or equal to, the detection interval. Note that the cardiac intervals are the times between atrial events for analysis of atrial arrhythmias, and the times separating ventricular events for analysis of ventricular arrhythmias.

Arrhythmia detection is comprised of detectors of three types of arrhythmia events, listed in their order of priority: fibrillation, tachycardia, and the onset of tachycardia. If the history of cardiac events meets the criteria for more than one type of arrhythmia, the device classifies the event in the higher priority detector. This preliminary classification of arrhythmia events is one factor for defining an appropriate arrhythmia reversion therapy.

In one operation of arrhythmia detection analysis, a fibrillation detector block 103 recognizes the possibility of ventricular fibrillation when the cardiac output falls to a very low level (for example, 40% of the standard or normal value) within a short time. Therefore, if COavg is less than a predetermined fibrillation-associated percentage of COstd, then the pacer performs rapid discrimination of ventricular fibrillation, as controlled by ventricular fibrillation logic block 104, and immediately performs shock therapy in deliver shock block 105 to revert the pathological condition. The pacer operates in this manner whether it detects arrhythmias by analyzing cardiac output alone or in conjunction with heart rate.

If the pacer 10 is configured to detect arrhythmias by analyzing cardiac output in conjunction with heart rate, the fibrillation detector block 103 also analyzes heart rate using the aforementioned X/Y detector, which compares the current heart rate to a preselected fibrillation detection interval (FDI). In the preferred embodiment of the invention, FDI is a fixed value of 250 ms and the X/Y detector criterion is 8 short intervals out of 10 cardiac cycles. If the X/Y detection criterion is met and COavg is not less than the previously discussed predetermined percentage of COstd, then a possible ventricular fibrillation condition exists (shown by the "yes" state of fibrillation arrhythmia condition block 106). Accordingly, the pacer logs the possible ventricular fibrillation condition state identifier in log fibrillation condition block 107, and then executes arrhythmia confirmation block 115. Otherwise (i.e., a "no" state in block 106), the pacer examines cardiac output and heart rate to determine whether a tachycardia condition exists in tachycardia detector block 108.

If the antitachycardia pacemaker 10 is configured in a dual chamber mode, rather than a single chamber mode, the fibrillation detector block 103 of FIG. 12 performs a second fibrillation analysis operation, detection of atrial fibrillation. Referring back to FIG. 9 for a moment, a missing or reduced amplitude Doppler A wave 98 indicates atrial fibrillation. Therefore, if the A wave amplitude falls to a very low level (for example, 40% of the average or below) within a short time (for example, 15 seconds), the atrial fibrillation detector of the pacer recognizes the possibility of atrial fibrillation. This is shown in FIG. 12 by the "yes" state of fibrillation arrhythmia condition block 106. Accordingly, the pacer logs the possible atrial fibrillation condition state identifier in log fibrillation condition block 107, and then executes arrhythmia confirmation block 115. Otherwise (i.e., a "no" state in block 106), the pacer tests for the presence of a tachycardia condition in tachycardia detector block 108.

Tachycardia detector block 108 identifies the possibility of a pathological tachycardia condition when the cardiac output falls to a moderately low level (for example, 75% of the standard value). When COavg is less than a predetermined tachycardia-related percentage of COstd, then the tachycardia detector recognizes the possibility of pathological tachycardia (shown by the "yes" state of tachycardia arrhythmia condition block 109) and the pacer logs the possible pathological tachycardia condition state identifier in log tachycardia condition block 110, and then executes arrhythmia confirmation block 115.

If the pacer 10 is configured to analyze cardiac output in combination with heart rate, the tachycardia detector block 108 appraises heart rate using the X/Y detector, which compares each cardiac interval of a recent history of intervals to a preselected Tachycardia Detection Interval (TDI). TDI limits range from 300 ms to 600 ms, defining tachycardia rates from 200 to 100 bpm, respectively. A tachycardia condition may be either pathological or physiological, as occurs when the patient is exercising. To distinguish pathological tachycardias, the pacer analyzes the cardiac output measurement. If the cardiac output (COavg) is less than some preset threshold level (for example, 75%) of the standard value (COstd) and the cardiac interval is shorter than TDI, the pacer classifies the tachycardia as pathological. Accordingly, the pacer logs the possible pathological tachycardia condition state identifier in log tachycardia condition block 110, and then executes arrhythmia confirmation block 115. Cardiac output analysis allows the antitachycardia pacemaker to avoid unnecessary antitachycardia pacing when exercise or stress causes an elevated heart rate. If the heart rate history satisfies the X/Y detector criterion for tachycardia and the cardiac output remains normal, the pacer will not classify the condition as a possible pathological tachycardia and will, instead, analyze cardiac output and heart rate information to detect the onset of tachycardia in onset detector block 112.

The pacer 10 performs the operation of onset detector block 112 only when it is configured to analyze cardiac output in combination with heart rate. Otherwise, the pacer fails to detect an arrhythmia condition in this cardiac cycle and, under the control of rate detect enabled block 111, waits for the next cycle in wait block 100. Onset detector block 112 identifies a possibility of the onset of a tachycardia condition. A combination of a reduced cardiac output and a sudden and sustained decrease in interval duration triggers onset detection. In onset detector block 112, the pacer examines the cardiac interval history to perceive a sudden decrease in interval length while performing X/Y detection. A pathological tachycardia rhythm arises suddenly, often within two cardiac cycles. In contrast, a physiological tachycardia gradually increases in rate, usually accelerating one or two beats per minute (bpm) per cardiac cycle.

The onset detector block 112 first performs X/Y detection (for example, 12 of 15 or 16 of 20), in which the pacer compares each cardiac interval in a recent history of cardiac intervals to a predetermined Onset Detection Interval (ODI), having a range of 300 ms to 600 ms, to ascertain whether a decrease in interval length is sustained. ODI is normally a longer interval than TDI, to provide, by means of the tachycardia onset detector, faster pathological detection and response.

The onset detector block 112 stores interval lengths for a history of more than Y cardiac intervals, calculates an average cardiac interval at a point in the cardiac history preceding the Y intervals used for X/Y detection from the stored intervals, decrements this previous cardiac interval average by a predetermined delta value, then compares this decremented value to the current cardiac interval to determine whether a decrease in interval length is sudden (when the current interval is shorter than the previous average minus delta). After the interval history meets the suddenness criterion, the X/Y detector then verifies that all Y intervals remain at least delta shorter than the calculated average interval and that at least X out of Y intervals are also shorter than or equal to ODI. If not, the onset of tachycardia condition does not exist and the pacer fails to detect an arrhythmia condition in this cardiac cycle and, under the control of rate detect enabled block 111, waits for the next cycle in wait block 100.

The onset detector block 112 is similar in operation to the tachycardia detector block 108. It uses cardiac output measurements to distinguish pathological from physiological tachycardias. The purpose of cardiac output analysis in a tachycardia onset detector employing combined cardiac output and heart rate tests is to distinguish those tachycardias which are obviously physiological. The pacer does not perform arrhythmia confirmation block 115 for physiological tachycardias. If the cardiac rhythm meets the X/Y detector criterion for onset detection and the cardiac output value COavg is not greater than COstd by a predetermined percentage (for example, 25%), an arrhythmia condition exists (illustrated by a "yes" condition of onset arrhythmia condition block 113) and the pacer classifies the condition as a possible onset of tachycardia and logs the onset of tachycardia condition state in block 114 in nearly all cases. If the heart rate history satisfies the X/Y detector criterion for onset detection and the COavg is greater than COstd by the aforesaid predetermined percentage, the pacer reclassifies the condition as a non-arrhythmia event in onset arrhythmia condition block 113, after which pacer control returns to wait block 100.

In arrhythmia confirmation block 115, the antitachycardia pacer 10 confirms the presence of tachyarrhythmia before delivering each antitachycardia pacing (ATP) train or before delivering cardioversion/defibrillation shock. Tachyarrhythmia confirmation, like arrhythmia detection, includes analysis of cardiac output or cardiac output in combination with X/Y detector evaluation of heart rate.

If the pacer 10 is configured to detect cardiac arrhythmias based on cardiac output measurements alone, arrhythmia confirmation block 115 performs tests to confirm conditions of pathological tachycardia or atrial fibrillation (only for dual chamber sensing and therapy modes). The pacer continues to sample and integrate Doppler ultrasound waveforms to determine cardiac output and observe any changes in Doppler A wave (98, FIG. 9) amplitudes. If the pacer recognized the possibility of atrial fibrillation in fibrillation detection block 103 and the Doppler A wave amplitude continues to remain at a low level (for example, 40% of the average or below), the pacer confirms the presence of atrial fibrillation and, under control of an arrhythmia confirmed logic block 116, classifies the arrhythmia in block 117. If the pacer recognized the possibility of a pathological tachycardia in tachycardia detector block 108 and the updated COavg measurement remains less than the predetermined tachycardia-related percentage of COstd, then the pacer confirms the presence of a pathological tachycardia condition and, under control of an arrhythmia confirmed logic block 116, classifies the arrhythmia in block 117.

If the pacer 10 is configured to detect cardiac arrhythmias based on cardiac output measurements in combination with heart rate, arrhythmia confirmation block 115 performs tests to confirm conditions of pathological tachycardia, onset of pathological tachycardia, atrial fibrillation, or ventricular fibrillation. For arrhythmia confirmation using heart rate analysis, each confirmation test requires redetermination of a tachyarrhythmia confirmation interval (TCI), which the X/Y detector compares with the current cardiac interval to characterize heart rate. The TCI value depends on the identity of the detector recognizing the possibility of an arrhythmia condition. If a possible tachycardia onset condition is present, the pacer automatically sets TCI to the average interval before onset less a fraction of the predetemined delta parameter (for example, one-half). Otherwise, the pacer sets TCI equal to the tachycardia detection interval, TDI. In either case, TCI is limited to values between the onset detection interval, ODI, and TDI.

In the preferred embodiment of the invention, the X/Y detector criterion is 8 of 10 cycles for confirmation of ventricular fibrillation. Confirmation of other arrhythmias is based on a 5 of 6 criterion. The pacer 10 confirms the presence of an arrhythmia when the X/Y detection criterion identifies an arrhythmia and the updated cardiac output measurement (COavg) remains at a reduced level in comparison to the standard or normal cardiac output (COstd). In the case of atrial fibrillation confirmation, the Doppler A wave amplitude must remain at a reduced level to affirm the condition. If the pacer determines that either the cardiac output or heart rate fail to confirm an arrhythmia condition, it reclassifies the condition as a non-arrhythmia event in arrhythmia confirmed logic block 116, after which pacer control returns to wait block 100.

Upon confirming the presence of tachyarrhythmia but prior to delivering therapy, the pacer 10 classifies the arrhythmia in block 117 to determine an appropriate therapy. The pacer continues to sample and integrate Doppler ultrasound waveforms to determine cardiac output and observe any changes in Doppler A wave amplitudes. If the pacer is configured to detect arrhythmias based on heart rate in combination with cardiac output, it continues to perform rate monitoring and X/Y detection analysis.

If the pacer 10 is configured to detect cardiac arrhythmias based on cardiac output measurements alone, ventricular arrhythmia classification is based on the relationship of the updated cardiac output level, COavg, in comparison to the standard level, COstd. Atrial arrhythmia classification, for dual chamber pacing modes, is based on Doppler A wave levels. A physician can perform electrophysiological testing to determine the cardiac output levels associated with particular classifications of arrhythmias. From such testing, the physician preselects a number of therapies and associated COavg/COstd ratio boundaries, then programs codes reflecting these selections into the pacer using standard communication techniques. The pacer determines the COavg/COstd ratio to classify arrhythmias in block 117.

If the pacer is configured to detect cardiac arrhythmias based on cardiac output measurements in combination with heart rate, arrhythmia classification (block 117) is based on analysis using the X/Y detector in conjunction with two intervals of predetermined duration, a minimum tachycardia cycle length for antitachycardia pacing (TCLminATP) and a maximum tachycardia cycle length for defibrillation (TCLmaxD). TCLminATP represents the tachycardia cycle length below which intervals are too short for antitachycardia pacing to be effective. TCLmaxD represents the tachycardia cycle length below which the patient is hemodynamically compromised by the tachyarrhythmia and, therefore, requires shock therapy. TCLminATP and TCLmaxD vary as a function of the relationship of COavg to COstd. Note that TCLmaxD must always be greater than TCLminATP. There can be no range of interval lengths which are too short for antitachycardia pacing but too long for shock therapy.

Figure 13A:
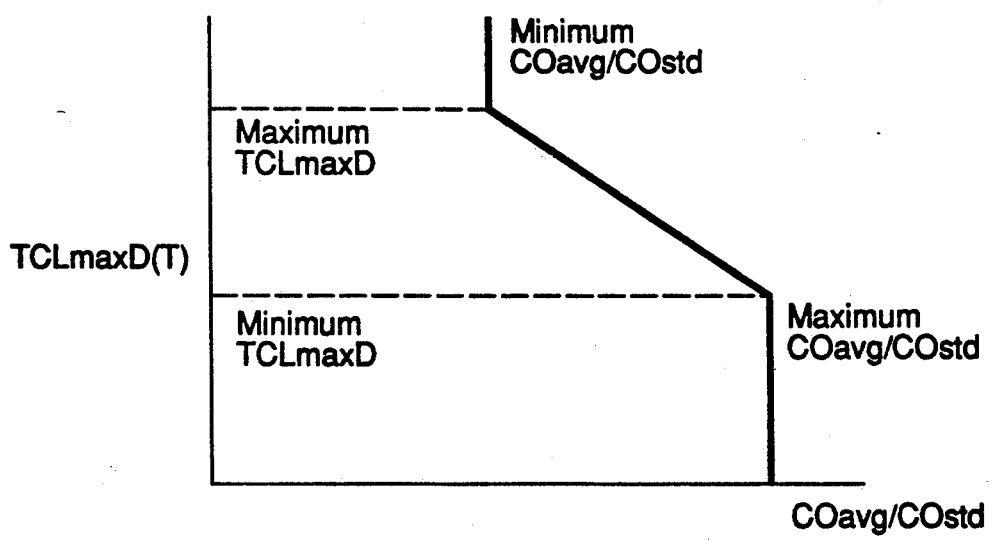
FIGS. 13A and 13B set forth graphic representations of a means for automatically determining, from cardiac output measurements, tachycardia cycle length boundary limits used in classifying arrhythmias as fibrillation and tachycardias, respectively.
Figure 13B:
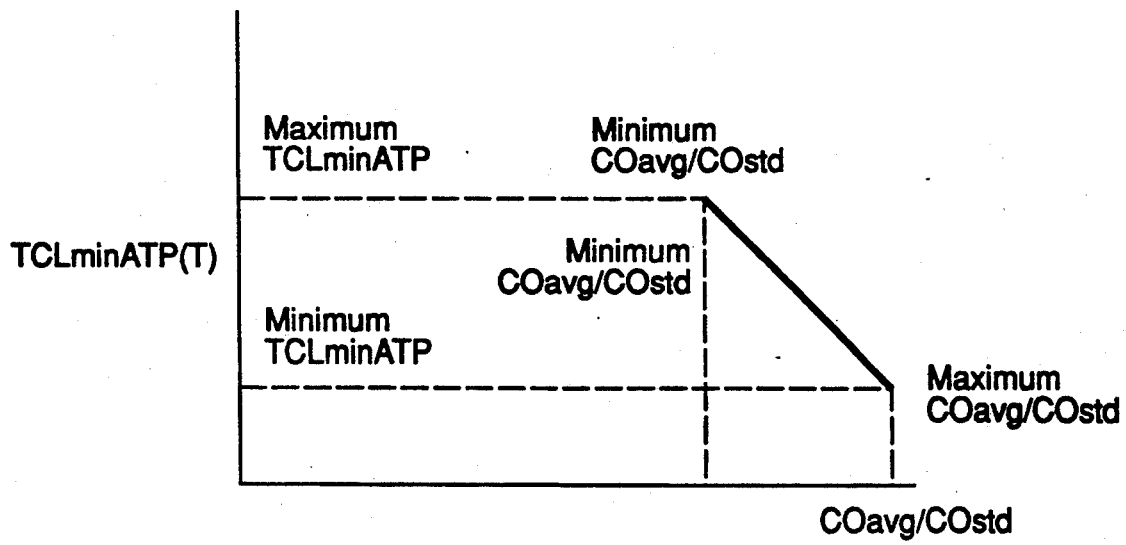

Referring to FIGS. 13A and 13B, graphic representations are set forth therein of a means for automatically determining, from cardiac output measurements, tachycardia cycle length boundary limits used in classifying arrhythmias as fibrillations and tachycardias, respectively. More particularly, FIGS. 13A and 13B illustrate the manner for determining TCLmaxD and TCLminATP, respectively, from COavg and COstd. While a very high cardiac rate is some evidence of fibrillation, the precise rate characterizing fibrillation may vary from time to time in a given patient. Accordingly, a second means for identifying fibrillation is desirable to confirm actual fibrillation conditions while avoiding the danger and discomfort associated with generating unnecessary shocks.

A much reduced cardiac output (for example, a degradation by 40% or more) is always associated with fibrillation. Therefore, the pacer 10 classifies a rhythm as fibrillation for all heart rates having such a reduced cardiac output. Less severe reductions in cardiac output are evidence of fibrillation. In such cases the pacer analyzes heart rate for a further indication of the fibrillation condition. As shown in FIG. 13A, the illustrative embodiment of the invention derives TCLmaxD for the current ratio of COavg to COstd by linearly interpolating between two points defined by preselected TCLmaxD and COavg/COstd ratio maxima and minima. Each time the pacer updates COavg and COstd, it performs the linear interpolation as shown in FIG. 13A, to determine the operative TCLmaxD parameter for classifying cardiac rhythms as fibrillation and activating shock therapy. Referring to FIG. 11B, the pacer determines TCLminATP in a similar manner to the derivation of TCLmaxD except that preselected parameters, TCLminATP and COavg/COstd ratio maxima and minima, define TCLminATP limits. Preselected endpoint values must provide for the derivation of TCLmaxD values which are greater than TCLminATP values for all COavg/COstd ratios. This range of allowable values for TCLminATP and TCLmaxD is illustrated by the lower and upper broken lines in FIG. 14.

Figure 14:
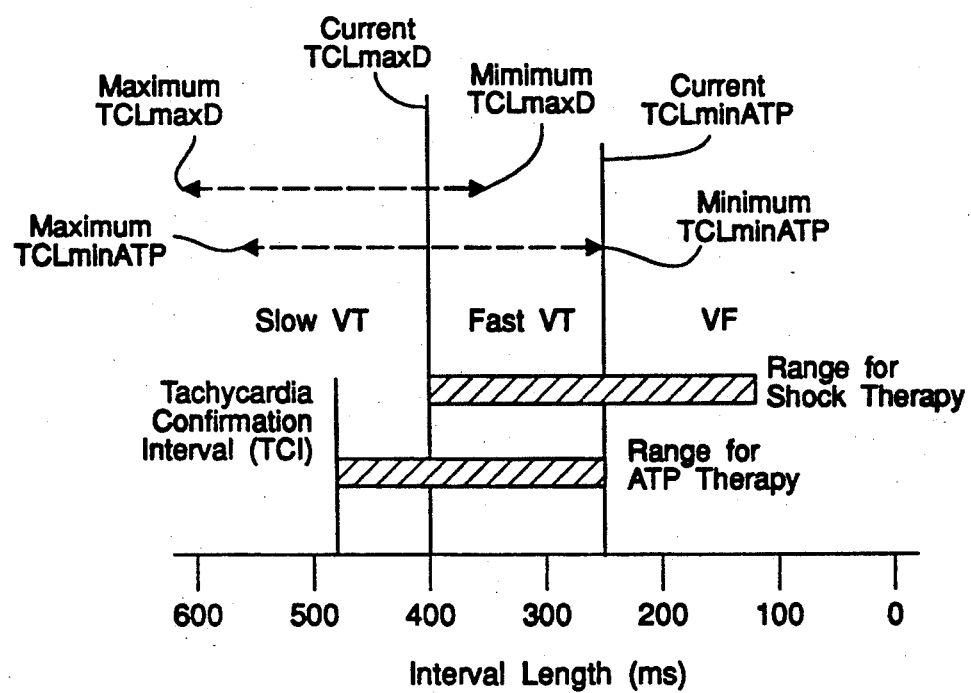
FIG. 14 is a graphic representation of tachycardia classifications as a function of the lengths of tachycardia cycle intervals.

Referring to FIG. 14, sensed cardiac intervals after the detection of an arrhythmia condition are called tachycardia cycle lengths (TCL). Tachyarrhythmias are grouped into a number of classifications by TCL - three in the preferred embodiment of the invention. Slow VT occurs when TCL is longer than the current TCLmaxD. The pacer 10 performs antitachycardia pacing, in deliver therapy block 119 (FIG. 12), only for tachyarrhythmias with a TCL between TCLmaxD and TCI. For cycle lengths longer than TCI, the pacer does not deliver a therapy, as controlled by therapy logic block 118, but instead directs pacer control to wait block 100. Fast VT arises when TCL is longer than the current TCLminATP and shorter than or equal to the current TCLmaxD. In deliver therapy block 119, the pacer initiates antitachycardia pacing for cycle lengths within this range, but may activate shock therapy if the abnormal rhythm is not reverted by pacing therapy. VF occurs when TCL is shorter than or equal to TCLminATP and when the cardiac output falls to very low levels (for example, COavg less than 40% of COstd). In either case the pacer only employs shock therapy. After delivering the selected therapy, pacer control returns to wait block 100.

When operating in a dual chamber antitachycardia pacing mode, the pacer 10 measures cardiac output not only to improve detection and classification of arrhythmias, but to provide better synchronization between ATP pulses generated in the atrium and ventricle. Cardiac output is an unambiguous indication of how well the needs of the body are satisfied. The antitachycardia pacer of the present invention uses the cardiac output parameter to indicate how well the heart is performing in response to, rather than in anticipation of, the hemodynamic status of the body. A-V delay is one of the parameters governing DDD pacing. Upon time-out of the V-A interval timer, or upon atrial sensing of an intrinsic atrial rate slower than the maximum atrial tracking rate, the pacemaker sets a timer to the A-V delay value. When the timer expires, unless pacing is inhibited by ventricular sensing prior to time-out, the pacemaker generates a stimulating pulse in the ventricle.

Figure 15:
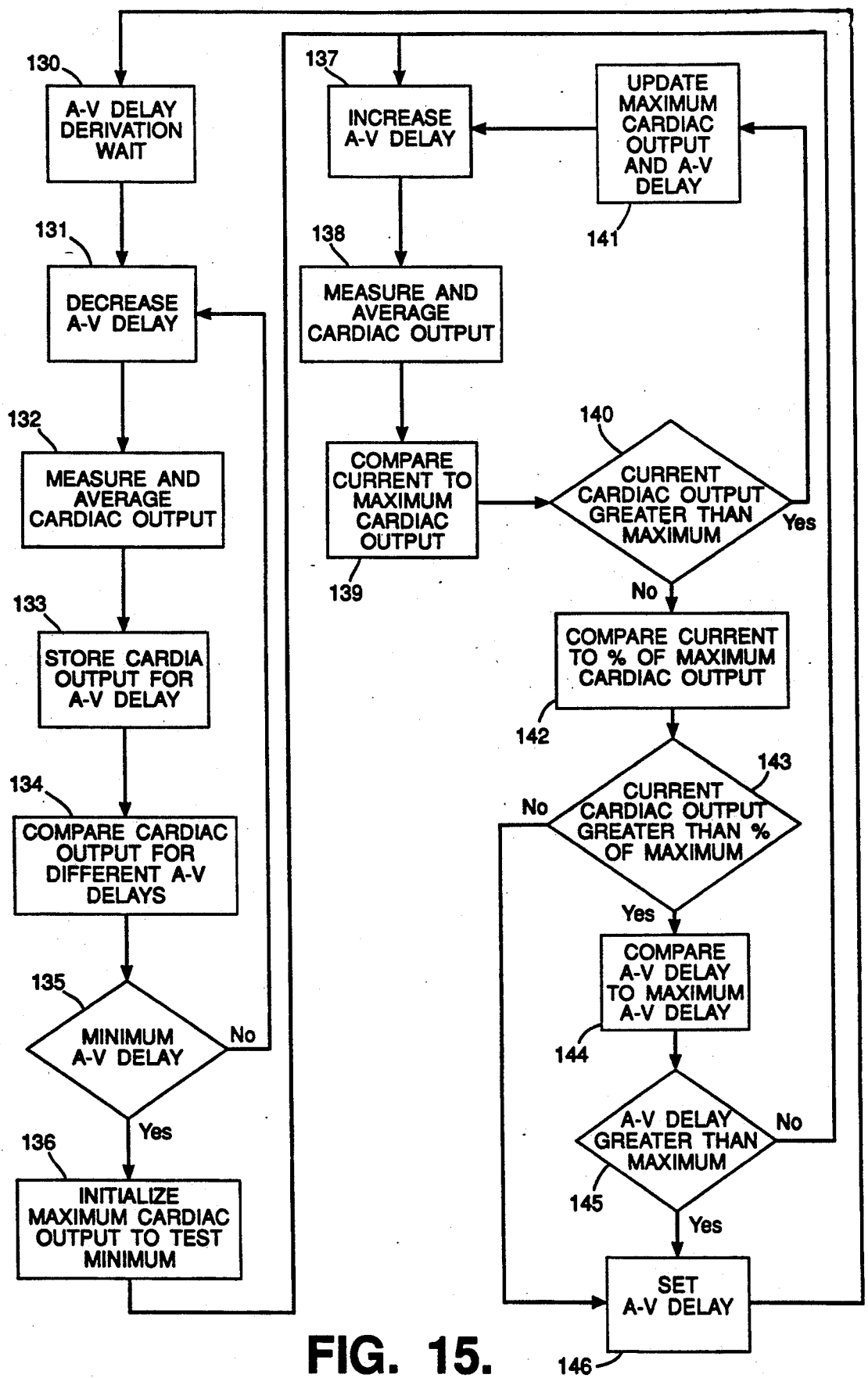
FIG. 15 is a flow chart illustrating the operational steps utilized in a procedure in accordance with the invention for setting an A-V delay parameter to an interval which optimizes cardiac output and the hemodynamic state of the body.

Referring to FIG. 15, the pacer 10 uses the cardiac output measurement to determine the heart's optimum A-V delay, the time interval between natural or stimulated atrial activity and the onset of a stimulation pulse generated in the ventricle which results in the maximum cardiac output. Upon activation of an A-V delay search operation at predetermined intervals or at the request of an external programming device, when operating in dual chamber bradycardia pacing mode and waiting in A-V delay derivation wait state in block 130, the pacer begins modulating the timing of electrical heart activity by decreasing the A-V delay interval in block 131, measuring and averaging cardiac output over a predetermined number of cardiac cycles in block 132, storing averaged cardiac output measurements according to each tested A-V delay interval in block 133, and comparing averaged cardiac output measurements for different A-V delay interval test conditions in block 134. The pacer performs blocks 131 through 134 until it reaches a predetermined minimum delay value, as controlled by block 135. The pacer measures and stores the minimum averaged cardiac output value, obtained during the present scan, and its associated A-V delay interval, in an initialize maximum cardiac output to test minimum block 136. This initializes the maximum cardiac output value to a low level.

The pacer 10 then gradually increases the A-V delay interval (block 137) and continues to measure and average the cardiac output for each interval over a number of cardiac cycles in block 138. The pacer compares the averaged cardiac output value associated with each A-V delay interval with the stored maximum cardiac output in block 139. If the current averaged cardiac output is larger than the stored maximum cardiac output, as controlled by logic block 140, the pacer stores the current averaged cardiac output value in the maximum cardiac output memory location and stores the current A-V delay identification in block 141, and then continues to increase the A-V delay by again increasing the A-V delay interval in block 137. If the current averaged cardiac output is not larger than the maximum cardiac output, according to logic block 140, then the pacer compares the current cardiac output value to a predetermined percentage (for example, 80%) of the maximum cardiac output in block 142. The pacer continues increasing the A-V delay and testing the cardiac output in blocks 137 to 145 until the cardiac output becomes less than the preset percentage of the maximum cardiac output measured during the current test (blocks 142 and 143), until natural ventricular heartbeats consistently inhibit ventricular pacing, or until the A-V delay is longer than a predetermined maximum value (blocks 144 and 145). The pacer sets the operational A-V delay to that interval associated with the maximum cardiac output in block 146.

Referring to FIG. 16, there is depicted in illustrative format one embodiment of an antitachycardia pacing algorithm according to the invention. It is to be understood that the antitachycardia pacer of the present invention does not limit the antitachycardia therapies to this algorithm but also includes any other algorithms known in the art. A series of M (M=4) pacing trains (a pacing train is a series of pacing spikes controllably delivered in rapid succession) are delivered. For train 1, the initial A-V delay interval, derived from the previously described analysis of cardiac output but shortened for the purposes of antitachycardia pacing, is 10 ms. During a ventricular tachycardia, the atrium and the ventricle are often in dissociation, therefore it is preferable for the dual chamber antitachycardia pacing to begin with a very short A-V delay interval in order to re-establish association or synchrony as soon as possible between both chambers of the heart. For this reason, the A-V delay, as established by cardiac output analysis, is lessened by a predetermined amount. The tachycardia cycle length (TCL) is 300 ms. The V-A delay interval (the ventricular to atrial interval) is calculated as a programmable percentage of the TCL for the purpose of adapting to the varying cycle lengths of tachycardias, and has been programmed to seventy percent of the TCL (300 ms) in this embodiment, thereby establishing the calculated V-A delay interval as 210 ms. In this embodiment, the percentage of the TCL is taken as an average over the four previous sensed intervals, and remains fixed at this value (210 ms) during the course of the therapy. For train 1, N=4, so that at the expiration of each of the 4 V-A delay intervals of 210 ms, an atrial pulse is delivered and at the expiration of each of the four A-V delay intervals of 10 ms a pulse is delivered to the ventricle, so that there are a total of N pairs of pulses (or 2N=8 pulses) delivered during train 1.

In train 2 of FIG. 16, the A-V delay interval has been programmed to increment in value from the low initial value of 10 ms in train 1 to the new value of 50 ms. The variation of the A-V delay interval is executed by computer software by standard methods known to those skilled in the art. In the same manner in trains 3 and 4 of FIG. 16, the A-V delay interval increases at the end of trains 2 and 3 to the increased values of 100 ms and 150 ms, respectively. In trains 2, 3, and 4, N=4, as in train 1, thereby delivering N (4) pairs of pacing pulses in each train. In this particular embodiment of the invention, the value of N is equal in all of the trains. However, N is a programmable parameter and may be programmed by the physician to suit the needs of a particular patient. Furthermore, N may have differing values for different trains in alternate embodiments of the invention.

As shown in FIG. 16, the A-V delay interval increments from 10 ms in train 1 to 150 ms in train 4. This parameter is also programmable and is patient dependent. The A-V delay may increment at the end of each train as in the preferred embodiment. However, the variation in the A-V delay is not necessarily limited to steady increments. It may include any combination of increases, plateaus and decreases in its value. Although it is preferable to include the variations at the end of each train, these may be executed at any time within a train and still fall within the scope of the invention. Preferably, the initial value A-V delay interval is less than or equal to 60 ms.

The V-A delay interval in the preferred embodiment is programmed as a percentage of the TCL (70%). Although the invention does not limit the V-A delay interval to a particular range, it has been found that the best results occur when it lies within the range of thirty percent to one hundred percent of the TCL. Furthermore, its value is not necessarily fixed during the antitachycardia therapy, but may vary and still remain within the scope of the invention. If it is programmed to vary, the initial value is a percentage of the TCL; for example a percentage of the average cycle length of the last four intervals of the detected tachycardia. For instance, the V-A delay interval may include various combinations of increasing, decreasing, or remaining at a fixed value. Any programmed variations may occur at the end of trains, or within trains, or may even be a function of A-V delay interval variations.

In FIG. 16 the number of trains M is 4. The number of trains is a patient-dependent, physician programmable parameter. At the completion of the M trains of antitachycardia pacing, the combined defibrillator pacing device 10 returns to its normal operating mode, including the options of normal dual chamber (DDD) pacing or defibrillation shocks, if necessary. Furthermore, the device may provide bradycardia support pacing, if required, which may include either single chamber or dual chamber bradycardia support pacing.

It will be apparent from the foregoing description that the present invention makes it possible to provide improved detection and classification of abnormal and harmful cardiac rhythms for the purpose of efficiently and safely performing antitachycardia pacing and defibrillation in an automatic implantable cardiac control system. The improved detection and classification of cardiac rhythms is achieved by employing an ultrasonic sensor, which is located outside the left heart, to measure the heart's cardiac output. On the basis of the cardiac output parameter, the present invention controls the administration and procedure of antitachycardia pacing and defibrillation therapy.

Although the invention has been described with reference to particular embodiments, it is to be understood that such embodiments are merely illustrative of the application of the principles of the invention. Hence numerous modifications may be made therein and other arrangements may be devised without departing from the true spirit and scope of the invention.

What is claimed is:

1. An antiarrhythmia pacing device for the reversion of cardiac arrhythmias comprising:
   means for generating stimulation pulses and adapted to deliver said pulses to a patient's heart,
   ultrasonic means adapted to be implanted within the patient's cardiovascular system for monitoring a cardiac output parameter corresponding to the volume of blood flow per unit of time within the cardiovascular system,
   means for deriving a cardiac output standard based on a time history of said cardiac output parameter,
   means for comparing said cardiac output parameter to said cardiac output standard,
   means responsive to said comparing means for detecting and classifying a pathological cardiac arrhythmia when said cardiac output parameter is less than at least one predetermined percentage of said cardiac output standard, and
   means responsive to said detecting means for controlling said generating means to operate in an antiarrhythmia pacing mode corresponding to said classification.

2. An antiarrhythmia pacing device according to claim 1, wherein said detecting means detects and classifies a pathological tachycardia condition and said controlling means controls said generating means to operate in an antitachycardia pacing mode.

3. An antiarrhythmia pacing device according to claim 1 in combination with an implantable pacemaker cardioverter/defibrillator device, wherein said classifying means classifies an arrhythmia as fibrillation when said cardiac output parameter is less than a second predetermined percentage of said cardiac output standard, said second predetermined percentage being lower than said one predetermined percentage, and wherein said detecting means issues a defibrillation signal to said controlling means upon detection of said fibrillation.

4. An antiarrhythmia pacing device according to claim 3, wherein said ultrasonic means is adapted to be implanted within the patient's right heart for ensonifying the patient's ascending aorta with ultrasonic energy and detecting returning ultrasonic energy reflected from blood cells within the ascending aorta.

5. An antiarrhythmia pacing device according to claim 1, wherein said ultrasonic means includes an ultrasonic transmitting means utilizing timed bursts of ultrasonic pulses, and an ultrasonic receiving means employing Doppler measurement techniques, for monitoring said parameter.

6. A dual chamber antitachycardia pacing device for the reversion of tachycardias comprising:
   means for generating atrial and ventricular stimulation pulses and adapted to deliver said pulses to a patient's atrium and ventricle, respectively,
   ultrasonic means adapted to be implanted within the patient's cardiovascular system for monitoring a cardiac output parameter corresponding to the volume of blood flow per unit of time within the cardiovascular system,
   means for deriving a cardiac output standard based on a time history of said cardiac output parameter,
   means for determining the patient's heart rate,
   analyzing means for comparing said cardiac output parameter to said cardiac output standard and for comparing said heart rate to a predetermined heart rate boundary,
   means responsive to the detection of a pathological tachycardia by said analyzing means for detecting a pathological tachycardia when said cardiac output parameter is less than a predetermined percentage of said cardiac output standard and said heart rate is faster than said predetermined heart rate boundary, and
   means responsive to the detection of a pathological tachycardia by said detecting means for controlling said generating means to operate in an antitachycardia pacing mode.

7. A dual chamber antitachycardia pacing device according to claim 6, further comprising:
   means for operating in a dual chamber bradycardia pacing mode, having an interval between atrial heartbeats and ventricular stimulation pulses, when the patient's heart is functioning with a below-normal natural rhythm,
   means for initiating an A-V delay test operating submode of said dual chamber bradycardia pacing mode,
   means responsive to the initiation of said A-V delay test operating submode for modulating the A-V delay between separate cardiac cycles,
   means for associating respective ones of said monitored cardiac output parameters with their corresponding operating submode A-V delay values, means responsive to said associating means for selecting an A-V delay associated with one of the largest cardiac output parameters, and means for terminating said A-V delay test operating submode and resuming operation in said dual chamber bradycardia pacing mode utilizing said selected A-V delay as the interval between atrial heartbeats and ventricular stimulation pulses.

8. A dual chamber antitachycardia pacing device according to claim 7, wherein, in said antitachycardia pacing mode, atrial and ventricular pacing pulses are generated and delivered in a series of pulse trains with each train consisting of a plurality of pacing pulses and with said ventricular and atrial pacing pulses being delivered in an alternating sequence to the ventricle and to the atrium, respectively.

9. A dual chamber antitachycardia pacing device according to claim 8, wherein said atrial and ventricular pulses being delivered in said alternating sequence are spaced apart by said selected A-V delay interval.

10. A dual chamber antitachycardia pacing device according to claim 6, wherein, in said antitachycardia pacing mode, atrial and ventricular pacing pulses are generated and delivered in a series of pulse trains with each train consisting of a plurality of pacing pulses and with said ventricular and atrial pacing pulses being delivered in an alternating sequence to the ventricle and to the atrium, respectively.

11. A dual chamber antitachycardia pacing device according to claim 6, in combination with an implantable pacemaker cardioverter/defibrillator device, wherein said predetermined percentage comprises a first predetermined percentage, and wherein said analyzing means detects fibrillation when said cardiac output is less than a second predetermined percentage of said cardiac output standard, said second predetermined percentage being lower than said first predetermined percentage, and wherein said detecting means issues a defibrillation signal to said controlling means upon detection of said fibrillation.

12. A dual chamber antitachycardia pacing device according to claim 11, wherein said ultrasonic means is adapted to be implanted within the patient's right heart for ensonifying the patient's ascending aorta with ultrasonic energy and detecting returning ultrasonic energy reflected from blood cells within the ascending aorta.

13. A dual chamber antitachycardia pacing device according to claim 6, wherein said ultrasonic means is adapted to be implanted within the patient's right heart for ensonifying the patient's ascending aorta with ultrasonic energy and detecting returning ultrasonic energy reflected from blood cells within the ascending aorta.

14. A dual chamber antitachycardia pacing device according to claim 6, wherein said ultrasonic means includes an ultrasonic transmitting means utilizing timed bursts of ultrasonic pulses, and an ultrasonic receiving means employing Doppler measurement techniques, for monitoring said parameter.

15. A method of detecting and reverting cardiac arrhythmias in an antiarrhythmia pacing device comprising the steps of:
activating an ultrasonic sensor implanted within a patient's cardiovascular system,
monitoring the output of said ultrasonic sensor to provide a cardiac output parameter corresponding to the volume of blood flow per unit of time within the cardiovascular system,
deriving a cardiac output standard based on a time history of said cardiac output parameters,
comparing said cardiac output parameter to said cardiac output standard,
detecting and classifying at least one pathological arrhythmia condition when said cardiac output parameter is less than at least one predetermined percentage of said cardiac output standard,
generating stimulation pulses for delivery within the patient's heart, and
controlling the timing and sequence of said pulse stimulations to operate in an antiarrhythmia pacing mode corresponding to said classification.

16. A method of detecting and reverting cardiac arrhythmias according to claim 15, wherein said detecting step detects and classifies a pathological tachycardia condition and said controlling means controls said generating means to operate in an antitachycardia pacing mode.

17. A method of detecting and reverting cardiac arrhythmias according to claim 15, further comprising the steps of:
detecting fibrillation when said cardiac output parameter is less than a second predetermined percentage of said cardiac output standard, said second predetermined percentage being lower than said one predetermined percentage, and
performing at least one operation of cardioversion or defibrillation in response to said fibrillation detecting step.

18. A method of detecting and reverting cardiac arrhythmias according to claim 15, wherein said step of activating an ultrasonic transducer includes the further steps of:
transmitting timed bursts of pulses into the patient's heart,
receiving ultrasonic echoes responding from said transmissions, and
analyzing said ultrasonic echoes using Doppler measurement techniques.

19. A method of detecting and reverting cardiac arrhythmias in a dual chamber antitachycardia pacing device comprising the steps of:
activating an ultrasonic sensor implanted within a patient's cardiovascular system,
monitoring the output of said ultrasonic sensor to provide a cardiac output parameter corresponding to the volume of blood flow per unit of time within the cardiovascular system,
deriving a cardiac output standard based on a time history of said cardiac output parameters,
determining the patient's heart rate,
comparing said cardiac output parameter to said cardiac output standard and comparing said heart rate to a predetermined heart rate boundary,
detecting a pathological arrhythmia when said cardiac output parameter is less than a predetermined percentage of said cardiac output standard and said heart rate is faster than said predetermined heart rate boundary,
generating stimulation pulses for delivery within the patient's atrium and ventricle, and
controlling the timing and sequence of said atrial and ventricular pulse stimulations to operate in an antiarrhythmia pacing mode.

20. A method of detecting and reverting cardiac arrhythmias according to claim 19, further comprising:

operating in a dual chamber bradycardia pacing mode, having an interval between atrial heartbeats and ventricular stimulation pulses, when the patient's heart is functioning with a below-normal natural rhythm, initiating an A-V delay test operating submode of said dual chamber bradycardia pacing mode, modulating the A-V delay between separate cardiac cycles following initiation of said A-V delay test operating submode, associated respective ones of said monitored cardiac output parameters with their corresponding operating submode A-V delay values, selecting an A-V delay associated with one of the largest cardiac output parameter based on said associating step, and terminating said A-V delay test operating submode and resuming operation in said dual chamber bradycardia pacing mode utilizing said selected A-V delay as the interval between atrial heartbeats and ventricular stimulation pulses.

21. A method of detecting and reverting cardiac arrhythmias according to claim 20, wherein, said antiarrhythmia pacing mode is an antitachycardia pacing mode, and wherein atrial and ventricular pacing pulses are generated and delivered in a series of pulse trains with each train consisting of a plurality of pacing pulses and with said ventricular and atrial pacing pulses being delivered in an alternating sequence to the ventricle and to the atrium, respectively.

22. A method of detecting and reverting cardiac arrhythmias according to claim 21, wherein said atrial and ventricular pulses being delivered in said alternating sequence are spaced apart by said selected A-V delay interval.

23. A method of detecting and reverting cardiac arrhythmias according to claim 20 wherein said antiarrhythmia pacing mode includes the sub-steps of:
measuring the cycle length of the tachycardia,
determining a V-A interval value less than or equal to the tachycardia cycle length,
delivering a pulse to the ventricle,
determining an initial value of an A-V delay interval as a function of said selected A-V delay interval,
delivering a pulse to the atrium at the expiration of said determined V-A interval value,
delivering a pulse to the ventricle at the expiration of said A-V interval value,
repeating pulse delivery to the atrium and the ventricle until the expiration of N V-A intervals and N A-V intervals thereby completing a first train of pulses,
delivering a series of M trains of pulses similar to said first train of pulses, and
varying said A-V delay interval value from the initial value at least once prior to the completion of said series of M trains of pulses.

24. A method of detecting and reverting cardiac arrhythmias according to claim 19, wherein said antiarrhythmia pacing mode is an antitachycardia pacing mode, and wherein atrial and ventricular pacing pulses are generated and delivered in a series of pulse trains with each train consisting of a plurality of pacing pulses and with said ventricular and atrial pacing pulses being delivered in an alternating sequence to the ventricle and to the atrium, respectively.

25. A method of detecting and reverting cardiac arrhythmias according to claim 19, wherein said antiarrhythmia pacing mode is an antitachycardia pacing mode and includes the sub-steps of:
measuring the cycle length of the tachycardia,
determining a V-A interval value less than or equal to the tachycardia cycle length,
delivering a pulse to the ventricle,
determining an initial value of an A-V delay interval,
delivering a pulse to the atrium at the expiration of said determined V-A interval value,
delivering a pulse to the ventricle at the expiration of said A-V interval value,
repeating pulse delivery to the atrium and the ventricle until the expiration of N V-A intervals and N A-V intervals thereby completing a first train of pulses,
delivering a series of M trains of pulses similar to said first train of pulses, and
varying said A-V delay interval value from the initial value at least once prior to the completion of said series of M trains of pulses.

26. A method of detecting and reverting cardiac arrhythmias according to claim 19, wherein said predetermined percentage comprises a first predetermined percentage, and further comprising the steps of:
detecting fibrillation when said cardiac output is less than a second predetermined percentage of said cardiac output standard, said second predetermined percentage being lower than said first predetermined percentage, and
performing at least one operation of cardioversion or defibrillation in response to said detecting step.

27. A method of detecting and reverting cardiac arrhythmias according to claim 19, wherein said ultrasonic sensor is adapted to be implanted within the patient's right heart, and wherein said step of activating an ultrasonic transducer includes the sub-steps of ensonifying the patient's ascending aorta with ultrasonic energy, and detecting returning ultrasonic energy reflected from blood cells within the ascending aorta.

28. A method of detecting and reverting cardiac arrhythmias according to claim 19, wherein said step of activating an ultrasonic transducer includes the further steps of:
transmitting timed bursts of pulses into the patient's heart,
receiving ultrasonic echoes responding from said transmissions, and
analyzing said ultrasonic echoes using Doppler measurement techniques.

29. An antiarrhythmia pacing device for the reversion of cardiac arrhythmias comprising:
means for generating stimulation pulses and adapted to deliver said pulses to a patient's heart,
ultrasonic means adapted to be implanted within the patient's right heart for ensonifying the patient's ascending aorta with ultrasonic energy and detecting returning ultrasonic energy reflected from blood cells within the ascending aorta for monitoring a cardiac output parameter corresponding to the volume of blood flow per unit of time within the cardiovascular system,
means for deriving a cardiac output standard based on a time history of said cardiac output parameter,
means for comparing said cardiac output parameter to said cardiac output standard,
means responsive to said comparing means for detecting and classifying a pathological cardiac arrhythmia when said cardiac output parameter is less than at least one predetermined percentage of said cardiac output standard, and means responsive to said detecting means for controlling said generating means to operate in an antiarrhythmia pacing mode corresponding to said classification.

30. An antiarrhythmia pacing device according to claim 29, wherein said detecting means detects and classifies a pathological tachycardia condition and said controlling means controls said generating means to operate in an antitachycardia pacing mode.

31. An antiarrhythmia pacing device according to claim 29, in combination with an implantable pacemaker carioverter/defibrillator device, wherein said classifying means classifies an arrhythmia as fibrillation when said cardiac output parameter is less than a second predetermined percentage of said cardiac output standard, said second predetermined percentage being lower than said one predetermined percentage, and wherein said detecting means issues a defibrillation signal to said controlling means upon detection of said fibrillation.

32. A method of detecting and reverting cardiac arrhythmias in an antiarrhythmia pacing device comprising the steps of:

activating an ultrasonic sensor implanted within a patient's right heart, wherein said activating step includes the sub-steps of ensonifying the patient's ascending aorta with ultrasonic energy, and detecting returning ultrasonic energy reflected from blood cells within the ascending aorta, monitoring the output of said ultrasonic sensor to provide a cardiac output parameter corresponding to the volume of blood flow per unit of time within the cardiovascular system, deriving a cardiac output standard based on a time history of said cardiac output parameters, comparing said cardiac output parameter to said cardiac output standard, detecting and classifying at least one pathological arrthythmia condition when said cardiac output parameter is less than at least one predetermined percentage of said cardiac output standard, generating stimulation pulses for delivery within the patient's heart, and controlling the timing and sequence of said pulse stimulations to operate in an antiarrhythmia pacing mode corresponding to said classification.

33. A method of detecting and reverting cardiac arrhythmias according to claim 32, wherein said detecting step detects and classifies a pathological tachycardia condition and said controlling means controls said generating means to operate in an antitachycardia pacing mode.

34. A method of detecting and reverting cardiac arrhythmias according to claim 32, further comprising the steps of:

detecting fibrillation when said cardiac output parameter is less than a second predetermined percentage of said cardiac output standard, said second predetermined percentage being lower than said one predetermined percentage, and performing at least one operation of cardioversion or defibrillation in response to said fibrillation detecting step.

* * * * *